(12) United States Patent
Van Wie et al.

(10) Patent No.: US 12,674,129 B2
(45) Date of Patent: Jul. 7, 2026

(54) MINIATURIZED CENTRIFUGAL BIOREACTOR AND ROTOR SYSTEM

(71) Applicant: Washington State University, Pullman, WA (US)

(72) Inventors: Bernard J. Van Wie, Pullman, WA (US); Kitana M. Kaiphanliam, Pullman, WA (US); Eric S. Barrow, Pullman, WA (US)

(73) Assignee: Washington State University, Pullman, WA (US)

( * ) Notice: Subject to any disclaimer, the term of this patent is extended or adjusted under 35 U.S.C. 154(b) by 1166 days.

(21) Appl. No.: 17/527,926

(22) Filed: Nov. 16, 2021

(65) Prior Publication Data

US 2022/0154125 A1      May 19, 2022

Related U.S. Application Data

(60) Provisional application No. 63/114,934, filed on Nov. 17, 2020.

(51) Int. Cl.
*C12M 3/04* (2006.01)
*C12M 1/00* (2006.01)

(52) U.S. Cl.
CPC ............ *C12M 27/10* (2013.01); *C12M 29/26* (2013.01)

(58) Field of Classification Search
CPC ....... C12M 27/10; C12M 29/26; C12M 33/10
See application file for complete search history.

(56) References Cited

U.S. PATENT DOCUMENTS 2,616,619 A * 11/1952 Macleod ............... B04B 5/0442
                                                        209/208
3,347,454 A      10/1967 Bellamy, Jr. et al.
(Continued)

FOREIGN PATENT DOCUMENTS

DE        2717344 A1      2/1987
FR        2392725 A1      12/1978
(Continued)

OTHER PUBLICATIONS

Cortesini, R., "What are the Ethical and Social Implications of Artificial Organs?," Wiley Online Library, Fourth Congress of the International Society for Artificial Organs, Nov. 14-17, 1983, Kyoto, Japan, 2 pages.

(Continued)

*Primary Examiner* — William H. Beisner
*Assistant Examiner* — Danielle B Henkel
(74) *Attorney, Agent, or Firm* — Lee & Hayes, P.C.

(57) ABSTRACT

A centrifugal bioreactor includes a turntable assembly, an electric motor coupled to the turntable assembly, and a replaceable rotor assembly coupled to the turntable assembly. The replaceable rotor assembly includes a plurality of reaction chambers that house cell cultures. A fresh medium tank holds fresh medium for the cell cultures, a spent medium tank holds a first portion of spent medium produced by the cell cultures, and an inoculation tank combines the fresh medium from the fresh medium tank and a second portion of the spent medium. A gas exchanger exposes the fresh medium and the second portion of the spent medium to gas. Additionally, a first pump supplies the fresh medium and the second portion of the spent medium to the plurality of the reaction chambers, and a second pump discard the first portion of the spent medium to the spent medium tank.

12 Claims, 11 Drawing Sheets

(56)                References Cited

U.S. PATENT DOCUMENTS

| | | | |
|---|---|---|---|
| 3,737,096 A | | 6/1973 | Jones et al. |
| 3,748,101 A | | 7/1973 | Jones et al. |
| 3,825,175 A | | 7/1974 | Sartory |
| 3,862,715 A | | 1/1975 | Remenyik |
| 3,955,755 A | | 5/1976 | Breillatt, Jr. et al. |
| 3,986,442 A | | 10/1976 | Khoja et al. |
| 4,010,894 A | | 3/1977 | Kellogg et al. |
| 4,056,224 A | * | 11/1977 | Lolachi ............... A61M 1/3696 |
| | | | 494/21 |
| 4,113,173 A | | 9/1978 | Lolachi |
| 4,127,231 A | | 11/1978 | Khoja et al. |
| 4,132,349 A | | 1/1979 | Khoja et al. |
| 4,146,172 A | | 3/1979 | Cullis et al. |
| 4,322,298 A | * | 3/1982 | Persidsky ............ G01N 33/491 |
| | | | 494/21 |
| 4,591,445 A | | 5/1986 | Spinell et al. |
| 4,798,579 A | * | 1/1989 | Penhasi ................... F16D 1/112 |
| | | | 494/56 |
| 4,939,087 A | | 7/1990 | Van Wie et al. |
| 5,122,284 A | * | 6/1992 | Braynin ............... G01N 33/491 |
| | | | 436/63 |
| 6,133,019 A | * | 10/2000 | Herman ................. C12M 41/00 |
| | | | 435/813 |
| 2007/0148764 A1 | * | 6/2007 | Suzuki ................... C12M 41/48 |
| | | | 435/293.1 |
| 2012/0270717 A1 | * | 10/2012 | Mehta ................... C12M 33/10 |
| | | | 494/12 |
| 2020/0297911 A1 | * | 9/2020 | Fitzpatrick ......... A61M 39/1011 |

FOREIGN PATENT DOCUMENTS

| | | |
|---|---|---|
| FR | 2395785 A1 | 1/1979 |
| SE | 7708858 | 2/1979 |

OTHER PUBLICATIONS

Dorin, Mel, et al., "Principles of Continuous Flow Centrifugation," Beckman Coulter, Inc., downloaded from https://www.beckman.com/resources/reading-material/application-notes/principles-of-continuous-flow-centrifugation, Apr. 10, 2025, 31 pages.

* cited by examiner

| CENTRIFUGAL BIOREACTOR (CBR) 100 | | |
|---|---|---|
| PROCESSOR(S) 122 | ROTOR ASSEMBLY 106 | SENSOR(S) 128 |
| MEMORY 124<br>SENSOR DATA 130<br>SETTING(S) 126 | MOTOR(S) 108 | TANK(S) 112 |
| | FLUID LINE(S) 120 | GAS EXCHANGER 114 |
| TURNTABLE ASSEMBLY 118 | PUMP(S) 116 | USER INTERFACE 132 |

102
104(1)
104(2)
104(3)
110(1)
110(2)
110(3)

Y
Z
X

1100 —

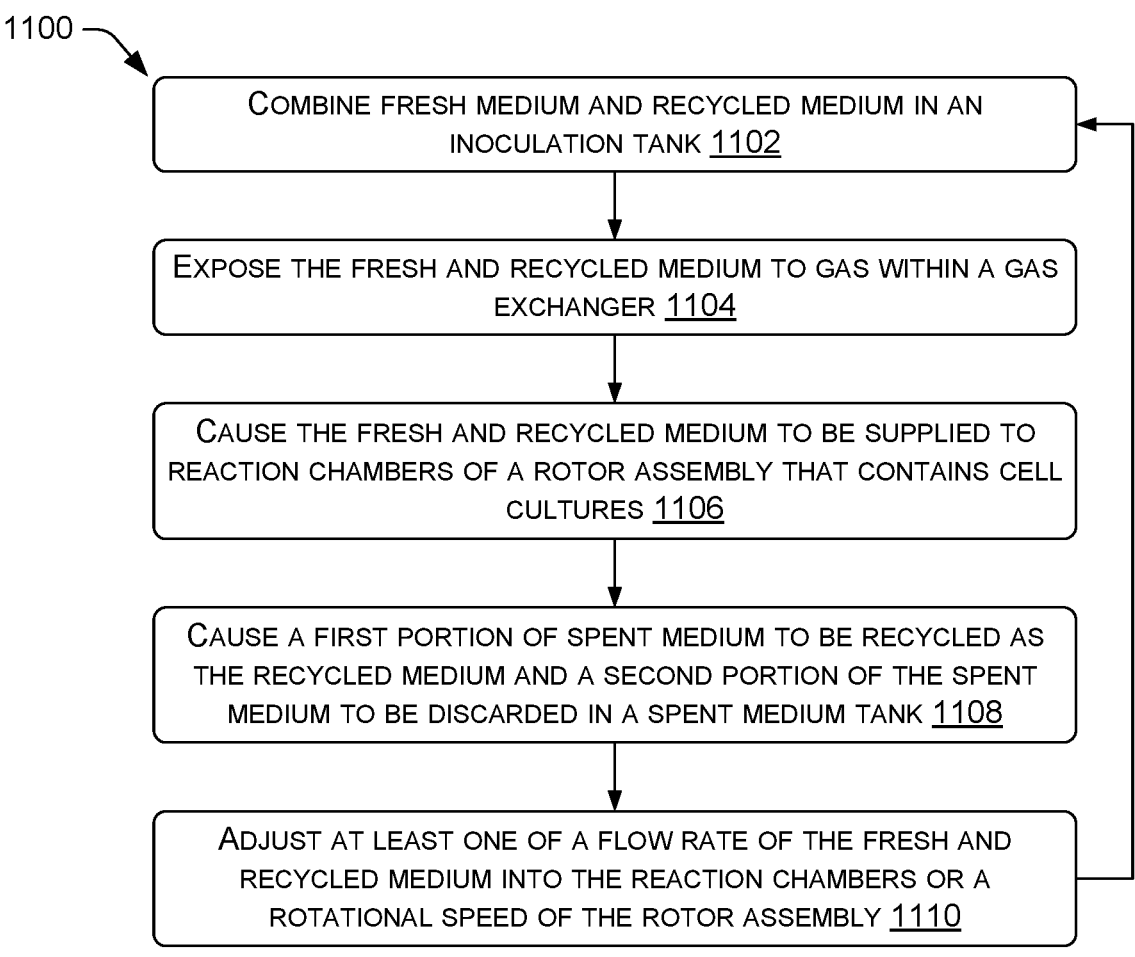

COMBINE FRESH MEDIUM AND RECYCLED MEDIUM IN AN INOCULATION TANK 1102

EXPOSE THE FRESH AND RECYCLED MEDIUM TO GAS WITHIN A GAS EXCHANGER 1104

CAUSE THE FRESH AND RECYCLED MEDIUM TO BE SUPPLIED TO REACTION CHAMBERS OF A ROTOR ASSEMBLY THAT CONTAINS CELL CULTURES 1106

CAUSE A FIRST PORTION OF SPENT MEDIUM TO BE RECYCLED AS THE RECYCLED MEDIUM AND A SECOND PORTION OF THE SPENT MEDIUM TO BE DISCARDED IN A SPENT MEDIUM TANK 1108

ADJUST AT LEAST ONE OF A FLOW RATE OF THE FRESH AND RECYCLED MEDIUM INTO THE REACTION CHAMBERS OR A ROTATIONAL SPEED OF THE ROTOR ASSEMBLY 1110

FIG. 11

MINIATURIZED CENTRIFUGAL BIOREACTOR AND ROTOR SYSTEM

CROSS-REFERENCE TO RELATED APPLICATIONS

This application claims priority to U.S. Provisional Application No. 63/114,934, filed Nov. 17, 2020, entitled "Miniaturized Centrifugal Bioreactor and Rotor System," the entirety of which is herein incorporated by reference.

GOVERNMENT LICENSE RIGHTS

This invention was made with government support under grant number 1645249 awarded by National Science Foundation. The government has certain rights in the invention.

BACKGROUND

Cellular immunotherapy takes advantage of a patient's natural immune response to effectively target cancer cells and other maladies. For example, a patient's T cells may be modified to express chimeric antigen receptors (CAR) specific to malignant cells. Existing immunotherapy techniques require a lengthy culturing process to condition a patient's donor cells, such as cytotoxic T lymphocytes (CTLs) cells. Static culturing, for example, is one method to grow cells and involves specialized flasks supplied with gas and nutrients. However, static culturing may take upwards of a month to produce enough cells for a single treatment cycle. Additionally, conventional techniques are not widely available and require specialized facilities. This limits access to immunotherapy techniques and increases a cost of such treatment.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features. The systems depicted in the accompanying figures are not to scale and components within the figures may be depicted not to scale with each other.

FIG. 11 illustrates an example process for growing cells within a reaction chamber, according to an example of the present disclosure.

DETAILED DESCRIPTION

Figure 1:
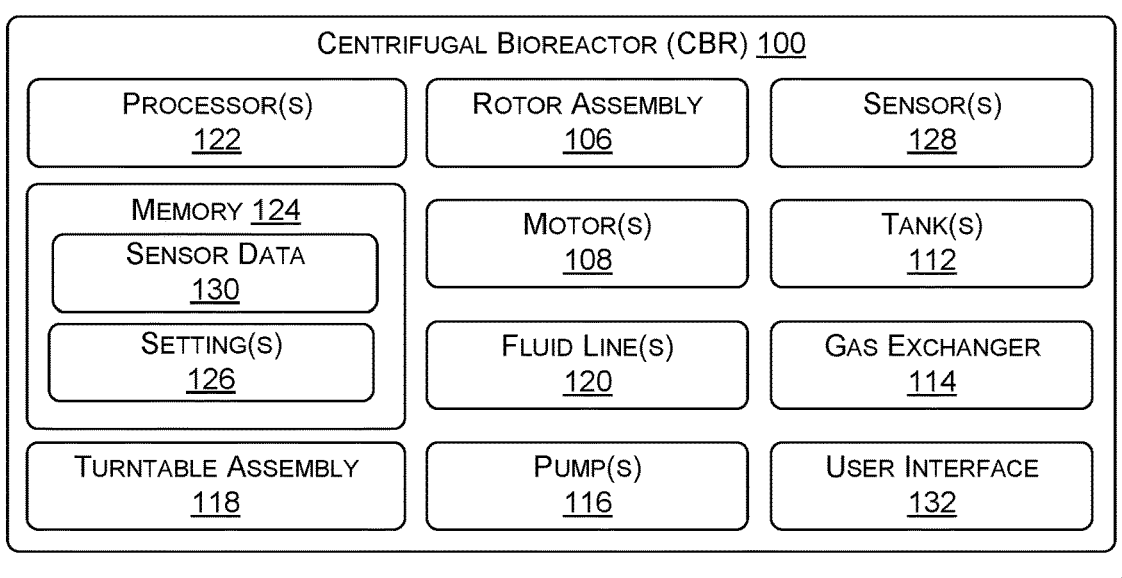
FIG. 1 illustrates a perspective view of an example centrifugal bioreactor (CBR) for immunotherapy cell culturing, showing selected components of the CBR, according to an example of the present disclosure.

This disclosure relates to a centrifugal bioreactor (CBR) for use in immunotherapy cell culturing. In some instances, the CBR includes a turntable assembly, a rotor assembly coupled to the turntable assembly, and an electric motor coupled to the turntable assembly for rotating the rotor assembly. The rotor assembly includes reaction chambers within which cells are cultured. For example, a cell culture may be placed within the reaction chambers and centrifuged to grow the cell culture. Lines fluidly couple to the rotor assembly, and more particularly, the reaction chambers for providing medium (e.g., nutrients, fluid, gases, etc.) to the cells. Lines also fluidly couple to the reaction chambers for discarding spent medium within the reaction chambers. One or more reservoirs are fluidly coupled to the rotor assembly for supplying the medium and storing the discarded medium. The CBR is capable of producing greater cell densities, in a shorter time than using conventional static culturing techniques, which not only improves access to immunotherapy cell culturing, but reduces expenses associated therewith. Additionally, the CBR may make immunotherapy cell culturing more widely available.

The CBR may include a housing within which components of the CBR reside. The housing may generally encapsulate the components to provide insulated environments for culturing the immunotherapy cells. In some instances, the housing may include separate compartments that house separate components of the CBR. Such separation may provide environments suitable for cell culturing and reduce chances of contamination. For example, a motor that rotates the rotor assembly may be located in a separate compartment from the rotor assembly to reduce heat being imparted to the cells (which may adversely impact cell growth). Moreover, user interfaces (e.g., touch panels) that are used by an operator to control an operator of the CBR may be located in a separate compartment to avoid contamination.

Generally, the rotor assembly represents a disc that defines a plurality of reaction chambers within which the cells are cultured. The reaction chambers may be shaped to suspend (e.g., centralize, retain, position, etc.) the cells therewithin. For example, the reaction chambers may include an isosceles trapezoid shape (e.g., kite-like shape). A supply line fluidly connects to the reaction chambers at an inlet of the reaction chamber, and a discharge line fluidly connects to the reaction chambers at an outlet of the reaction chamber. The supply line supplies medium to the reaction chambers for fostering immunotherapy cell growth. The discharge line, meanwhile, discards spent medium from the reaction chambers to get rid of waste produced by the cell cultures (e.g., lactate, ammonium, etc.). In some instances, the supply line and the discard line may be replaceable to accommodate cell culturing between patients and reduce contamination. Additionally, the rotor assembly (with the reaction chambers) may be replaced and/or interchanged.

The shape of the reaction chambers serves to balance forces experienced by the cell cultures. For example, the kite-like shape may balance centrifugal forces experienced by the cell culture with drag and/or buoyant forces. More particularly, the rotation of the rotor assembly results in centrifugal force on the cell culture. As the medium is supplied into the reaction chambers, a velocity of the medium at least partially counteracts the centrifugal force. An outward tapering of the reaction chambers slows the velocity of the medium within the reaction chambers. This velocity creates drag and buoyant forces on the cell culture. The outward taper causes that velocity to decrease as flow proceeds inward till the drag and buoyant forces inward are exactly counterbalanced by the centrifugal force outward caused by rotation of the rotor disk in which the chamber is housed. This counterbalancing of forces serves to center the cell culture suspension within the reaction chamber. As flow proceeds towards the outlet, however, the reaction chamber tapers inward. The inward tapering reduces a cross-sectional dimension of the reaction chamber and results in an increased fluid velocity.

In some instances, suspending the cell culture within the reaction chamber serves to increase a growth rate of the cells. For example, suspending the cell culture permits the cells to be exposed to the medium flowing through the reaction chambers. Comparatively, if the cells reside against a sidewall of the reaction chambers and/or allow to settle, some of the cells within the culture may not be exposed to the medium and, as a result, fail to grow or have a stymied growth. Suspending the cell culture within the reaction chambers may further serve to continuously expose the cell culture to fresh medium and nutrients, continuously discard spent medium and metabolites that inhibit cell growth, and/or balance forces to allow for uniform mixing of nutrients through the cross-sectional area.

In some instances, the rotor assembly may rotate between approximately 600 rotations per minute (RPM) and approximately 1400 RPM. Additionally, the medium may be supplied to the reaction chamber at a rate of approximately between 0.50 milliliters per minute (mL/min) and 1.0 mL/min. However, the flow rate of the medium and/or the centrifugal rate of the rotor assembly may be increased or decreased to optimize cell growth. For example, the centrifugal forces and the drag force and the buoyant force may be balanced to suspend (e.g., centralize) the cell culture within the reaction chamber. In other words, rotating the rotor assembly at a fast rate may suspend the cell culture within the reaction chambers as the cells grow in numbers and/or mass, for example. In some instances, the rate of rotation may be based at least in part on a cell size and density, the fluid density and viscosity, temperature, a percent or volume of cells in the reaction chambers and fluid in the chamber (e.g., number of cells inoculated into the CBR), and/or a density of the cells and the fluid with respect to percent volumes in the reaction chambers.

In some instances, the reaction chambers are supplied with fresh medium as well as recycled medium from the reaction chambers. A fresh medium tank, for example, may supply the fresh medium, and recycled medium may be combined with the fresh medium before being introduced into the reaction chambers. The recycle medium is received from the reaction chambers and then reintroduced back into the reaction chambers for further consumption by the cell cultures. This recycling may reduce a waste of nutrient resources and taking advantage of unconsumed nutrients within the medium. Provision of fresh medium serves to reduce the accumulation of toxic or inhibitory metabolites such as lactate and ammonium by removal of some of the medium in the effluent at a rate equivalent to the fresh feed rate to the process. In some instances, the fresh medium may be supplied at a rate of between approximately 0.025 mL/min and approximately 0.120 mL/min. In some instances, the recycled medium may be supplied at a rate of between approximately 0.55 mL/min and 1.20 mL/min. In some instances, the recycle rate may balance the centrifugal force within the reaction chambers. The fresh medium feed may be based on a recycle volume associated with an optimal dilution rate so the cells are refreshed with the necessary nutrients to grow while reducing metabolite concentrations, but the volumetric flow rate will not be so high that cells are "washed out" or, in other words, lost during expansion. However, in other examples, the fresh medium and/or the recycled medium may be supplied at greater or lesser rates and/or different ratios. Additionally, in some examples, the ratio of fresh medium to recycled medium may change over time.

Pump(s) supply the fresh and recycled medium to the reaction chambers. Additionally, pump(s) route a portion of the spent medium to a spent medium tank. For example, a first pump may feed the fresh and recycled medium into the reaction chambers to balance the centrifugal force, while a second pump may control fresh medium entering the inoculation tank and spent medium to the spent medium tank. In some instances, before being supplied to the reaction chambers, the fresh and recycled medium may pass through a gas exchanger. Within the gas exchanger, the medium may be exposed to carbon dioxide. The carbon dioxide serves to maintain a pH level (e.g., 7.2-7.4) of the fresh and recycled medium suitable for culturing the cell culture. Fluid lines route the medium to and from the reaction chambers, the pump(s), the tank(s), and so forth. The fluid lines may also connect to one or more anti-twist mechanisms to prevent the fluid lines from twisting, buckling, crimping and so forth during rotation of the rotor assembly. In additional, the CBR may include filtered air supplies containing oxygen needed for cell respiration and for fostering cell growth. The filtering of the air may remove contaminates or other harmful bacteria that may be detrimental to the cells being cultured.

The rotor assembly may have any number of reaction chambers, such as four, six, eight, and so forth. Individual reaction chambers may be diametrically opposed from one another such that the rotor assembly is balanced. A common feed line supplies the fresh and recycled medium to the reaction chambers, and a common spent medium line discards spent medium from the reaction chambers. In other words, the feed line may branch to supply the reaction chambers with the fresh and recycle medium, and the spent medium line may collect the spent medium from the individual reaction chambers. In some instances, the rotor assembly is capable of being interchangeable such that cells may be cultured between patients. For example, the rotor assembly may be easily decoupled and coupled to the CBR such that different patients' cells may be cultured within the CBR. The swappable nature of the rotor assembly permits continued use of the CBR with little downtime.

Although described herein as finding use in immunotherapy cell culturing, the CBR or the processes described herein may find use in other applications, such as monoclonal antibody production, production of secreted cell products, production of non-secreted products contained within cells, production of other cell types, or tissue engineering.

The present disclosure provides an overall understanding of the principles of the structure, function, device, and system disclosed herein. One or more examples of the present disclosure are illustrated in the accompanying drawings. Those of ordinary skill in the art will understand that the devices and/or the systems specifically described herein and illustrated in the accompanying drawings are non-limiting embodiments. The features illustrated or described in connection with one embodiment may be combined with the features of other embodiments. Such modifications and variations are intended to be included within the scope of the appended claims.

FIG. 1 illustrates an example centrifugal bioreactor (CBR) 100 for use in immunotherapy cell culturing. In some instances, the CBR 100 represents a continuous CBR that is configured to continuously rotate for immunotherapy cell culturing.

Generally, the CBR 100 includes a housing 102 within which components of the CBR 100 reside. In some instances, the CBR 100 includes three separate compartments 104 that house respective components of the CBR 100. A first compartment 104(1) may be associated with inoculating the immunotherapy cells, a second compartment 104(2) may house a rotor assembly 106, with reaction chambers (e.g., cavities, voids, etc.), for centrifuging and growing the immunotherapy cells, and a third compartment 104(3) may house motor(s) 108 that rotate the rotor assembly 106. Each of the compartments 104 are accessible via respective doors 110. A first door 110(1) provides and restricts access to the first compartment 104(1), a second door 110(2) provides and restricts access to the second compartment 104(2), and a third door 110(3) provides and restricts access to the third compartment 104(3). The doors 110 may represent hinged doors, or doors that slide on rails, tracks, and the like. In some instances, each of the compartments 104 are sealed from one another, such that within each of the compartments 104, a controlled environment is provided. Such sealing may prevent contamination to the cells being cultured. For example, the compartments may be environmentally and/or insulated from one another. The doors 110, or other components of the CBR 100, such as the rotor assembly 106, may be made of substantially transparent material to allow for optical detection of immunotherapy cells within the CBR 100.

In some instances, each of the compartments 104 may be controlled at a separate temperature, whether via respectively heating systems or a centralized system with ductwork, valves, dampeners, etc. Additionally, or alternatively, the compartments 104 may have separate HEPA-filtration unit that maintain a sterile environment. The compartments 104 may also include UV-C fluorescent bulbs for sterilization. For example, between uses or during use, the UV-C radiation may sterilize the one or more of the compartments 104.

The first compartment 104(1) may house tank(s) 112, a gas exchanger 114, and/or pump(s) 116 of the CBR 100. In some instances, the tank(s) 112 may include a fresh medium tank that houses (e.g., stores) fresh medium (e.g., nutrients) for the immunotherapy cells within reaction chambers of the rotor assembly 106. The tank(s) may also include an inoculation tank as well as a spent medium tank. Within the inoculation tank, fresh medium from the fresh medium tank may be combined with recycled medium from the reaction chambers. In some instances, the inoculation tank is seeded with modified cells with or without microbeads or protein scaffolds carrying antibodies for cell stimulation and activation (e.g., introducing of cell stimulants). Additionally, or alternatively, a circulation loop may be fitted to recycle antibody carrier such as microbeads or protein scaffolds or other growth stimulants. The inoculation tank therefore serves to combine fresh and recycled medium before medium is supplied to the reaction chambers. For example, by recycling the medium, glucose levels of the medium that is supplied to the reaction chambers is preserved. By combining the recycled medium with fresh medium, however, lactate and ammonium levels within the medium are diluted. In some instances, the glucose levels may be greater than twenty milligrams/deciliter (mg/dL). The glucose level may be ten times the Monod constant for any given cell line; the glucose level may be lower than this, however, that will decrease growth rates. Additionally, the lactate levels may be less than 750 mg/dL, or below the critical lactate concentration for a given cell line. In some instances, the ammonia levels may be less than 15 millimole/L, or below the critical ammonia concentration for any given cell line.

The spent medium tank receives spent medium from the reaction chambers for discarding. The spent medium tank receives a portion of the spent medium that is not recycled back into the inoculation tank. The tank(s) are capable of being interchangeable, or removable, from the CBR 100. For example, as the spent medium tank fills with spent medium, a new empty spent medium tank may be interchanged. Further, as the fresh medium is supplied, a new fresh medium tank may be interchanged to further supply fresh medium to the reaction chambers.

A gas exchanger 114 introduces carbon dioxide into the medium being supplied to the reaction chambers. The gas exchanger 114 may include gas-permeable tubing (e.g., silicone) through which the fresh and recycled medium routes, being combined in the inoculation tank. The gas exchanger may maintain approximately a five percent carbon dioxide level within the fresh and recycled medium to preserve a pH level of the fresh and recycled medium, as well as a dissolved oxygen (DO) level.

The pump(s) 116 may include a recycle pump that supplies fresh medium and recycled medium from the inoculation tank to the gas exchanger 114. From the gas exchanger 114, the recycle pump serves to supply the fresh medium and recycled medium to the reaction chambers. The pump(s) 116 also include a waste pump that directs a portion of the spent medium from the reaction chambers to the spent medium tank. In some instances, the pump(s) represent dynamic pumps (e.g., centrifugal pumps, axial pumps, etc.) and/or positive-displacement pumps (e.g., piston pumps, screw pumps, gear pumps, peristaltic pumps, etc.). In some instances, the peristaltic pumps accommodate replacement of single-use tubing and minimize risk of contamination between culturing immunotherapy cells amongst patients.

The second compartment 104(2) houses the rotor assembly 106 of the CBR 100. As explained herein, the rotor assembly 106 includes a plurality of reaction chambers within which the immunotherapy cells are cultured. The rotor assembly 106 rotates (e.g., about the Y-axis) within the second compartment 104(2). In some instances, the rotor assembly 106 couples to a turntable assembly 118 disposed in the second compartment 104(2). The rotor assembly 106 is capable of being interchanged with other rotor assemblies on the turntable assembly 118. The turntable assembly 118 mechanically couples to the motor(s) 108 that in some instances are disposed within the third compartment 104(3). For example, a belt, chain, or other linkages may mechanically couple the motor(s) 108 to the turntable assembly 118 for rotating (e.g., spinning) the rotor assembly 106. The motor(s) 108 may represent any suitable motors, such as a direct current (DC) brushless motor, a stepper motor, a series motor, and the like.

Components of the CBR 100 are fluidly connected together via one or more fluid lines 120. The fluid lines may route between the compartments 104, for example, to supply medium to the reaction chambers, as well as discharge medium from the reaction chambers. In some instances, the fluid lines may be rigid or flexible piping, conduits, and so forth. The fluid lines 120 may also supply gas to the gas exchanger 114. In some instances, the fluid lines 120 are capable of being interchanged with one another between culturing cells of different patients.

The CBR 100 is shown including various components to permit culturing of immunotherapy cells. For example, the CBR 100 is shown including processor(s) 122 and memory 124, where the processor(s) 122 may perform various functions and operations associated with culturing the immunotherapy cells, and the memory 124 may store instructions executable by the processor(s) 122 to perform the operations described herein. The processor(s) 122, for example, may control an operation of the pump(s) 116, the motor(s) 108, and so forth.

The memory 124 is shown storing, or having access to, setting(s) 126. The setting(s) 126 may be associated with operational parameters of the CBR 100, or components thereof. For example, the setting(s) 126 may be associated with or indicative of a speed of the pump(s) 116 (e.g., rotations per minute (rpm), a speed of the motor(s) 108, actuation of valves, and so forth. The processor(s) 122 communicate with the components of the CBR 100 for controlling the components in association with the setting(s) 126.

The CBR 100 is shown including sensor(s) 128. In some instances, the sensor(s) 128 may include encoders for measuring a rotational speed of the rotor assembly 106, humidity sensor(s) for measuring humidity within the compartments 104, flow rate sensor(s) for measuring a flow of medium (e.g., fresh and recycled, spent, and so forth) throughout the CBR 100, pressure sensor(s) for measuring pressure within the fluid lines, reaction actions, and so forth, and/or temperature sensor(s) for measuring temperature of the medium, temperature within the compartments 104, temperature within the reaction chambers, and so forth. The sensor(s) 128 may also include accelerometers that couple to the rotor assembly 106 for measuring an acceleration of the rotor assembly 106. Sensor(s) may also measure ammonium and/or lactate levels within the recycled medium may also be used to control flow rates of the fresh medium and/or the recycled medium.

In some instances, the sensor(s) 128 may include imaging sensors (e.g., cameras, light sensors, etc.) for measuring an amount of immunotherapy cells within the reaction chambers. For example, images of the reaction chambers may be captured, and the images may be analyzed for determining a density of immunotherapy cells within the reaction chambers. In some instances, the density of immunotherapy cells within the reaction chambers is indicative of whether the immunotherapy cells are ready for extraction from the CBR 100. Light sensors, for example, may be used to determine an amount of light capable of being passed through the immunotherapy cells and/or medium within the reaction chambers. If the amount of light is less than a threshold (e.g., light that is permitted to pass through near- or at-tissue density cultures), this may indicate that the immunotherapy cells are ready for harvesting. Comparatively, if the amount of light is greater than the threshold, this may indicate that the immunotherapy cells are not ready for harvesting. In some instances, a light source is strobed in a direction through the reaction chambers and images are captured for determining a cell density.

The sensor(s) 128 are configured to generate sensor data 130 that is stored in the memory 124. The processor(s) 122 are configured to utilize the sensor data 130 for at least partially controlling operations of the CBR 100. For example, the sensor data 130 may represent a flow rate of medium supplied to the reaction chambers. Based on the flow rate, the pump(s) 116 may either decrease or increase in speed to reduce or supply additional medium. As another example, based on the humidity and/or temperature within the compartments, coolers or heaters may be activated to produce an environment suitable for immunotherapy cell growth.

In some instances, the setting(s) 126 are input via a user interface 132. The user interface 132, for example, may display indications associated with the setting(s) 126, such as a speed of the pump(s) 116, motor(s) 108, how long to centrifuge the immunotherapy cells, and so forth. Through interacting with the user interface 132, a user, for example, may adjust the setting(s) 126. Additionally, or alternatively, in some instances, the setting(s) 126 are determined based at least in part on the sensor data 130. In some instances, the user interface 132 may represent a touch-sensitive display or other input/output devices for enabling adjustment of the setting(s) 126. The user interface 132 may also display the sensor data 130, such as a temperature. In some instances, the user interface 132 resides within the first compartment 104(1), external to the housing 102, and/or other locations that are accessible and/or viewable by a user of the CBR 100.

In some instances, the CBR 100 may be remotely controlled by one or more computing device(s), a remote system, and so forth. In such instances, the remote system may be located within an environment of the CBR 100 and/or remote from the environment. The remote system may further be implemented as one or more servers and may, in some instances, form a portion of a network-accessible computing platform implemented as a computing infrastructure of processors, storage, software, data access, etc. that is maintained and accessible via a network such as the Internet. Common expressions associated with the remote system include "on-demand computing", "software as a service (SaaS)", "platform computing", "network-accessible platform", "cloud services", "data centers", etc. The CBR 100 may be configured to communicate with the remote system via one or more networks. The network may represent any type of communication network, including a data network, and may be implemented using wired infrastructure (e.g., cable, CATS, fiber optic cable, etc.), a wireless infrastructure (e.g., RF, cellular, microwave, satellite, Bluetooth, etc.), and/or other connection protocols. In such instances, the CBR 100 is equipped with network interfaces to transmit to and receive data from the remote system.

The CBR 100 may additionally include air filters (e.g., HEPA) and/or fans for supplying oxygen, carbon dioxide, and/or other gases to the immunotherapy cells. The air filters may condition and sanitize the air before being supplied to the immunotherapy cells. The air filters may also filter air within each compartment 104. The CBR 100 may include other input and output (I/O) devices for controlling an operation of the CBR 100. For example, keyboards, microphones, speakers, light indicators, and the like may be included.

As used herein, a processor, such as the processor(s) 122 may include multiple processors and/or a processor having multiple cores. Further, the processor(s) may comprise one or more cores of different types. For example, the processor(s) may include application processor units, graphic processing units, and so forth. In one implementation, the processor(s) may comprise a microcontroller and/or a microprocessor. The processor(s) may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that may be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) may possess its own local memory, which also may store program components, program data, and/or one or more operating systems.

The memory 124 may include volatile and nonvolatile memory, removable and non-removable media implemented in any method or technology for storage of information, such as computer-readable instructions, data structures, program component, or other data. Such memory may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory may be implemented as computer-readable storage media ("CRSM"), which may be any available physical media accessible by the processor(s) to execute instructions stored on the memory. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Figure 2:
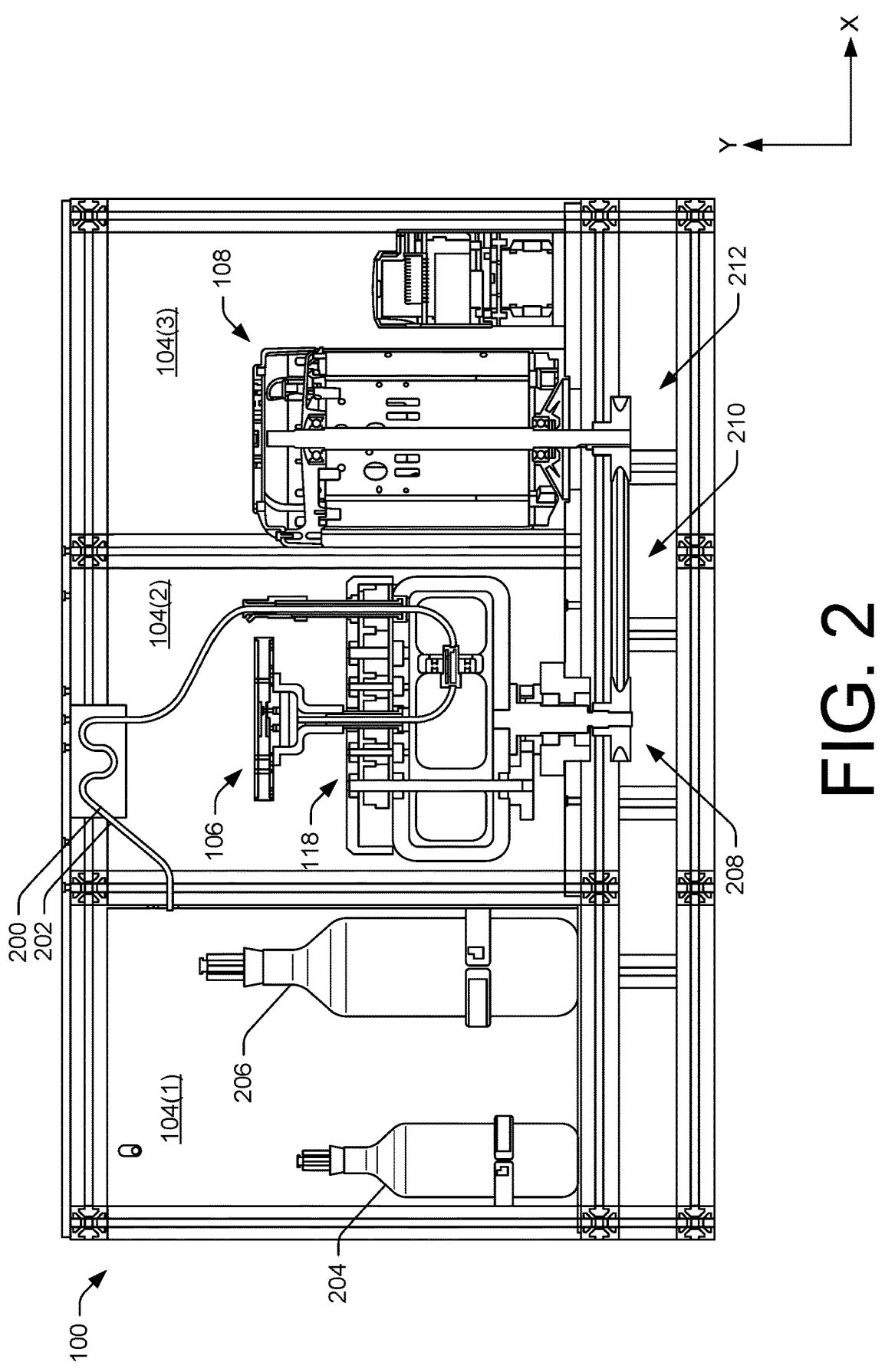
FIG. 2 illustrates a frontal view of the CBR of FIG. 1 with the access doors omitted for clarity, according to an example of the present disclosure.

FIG. 2 illustrates a front view of the CBR 100, showing the doors 110 removed to illustrate components within the compartments 104. As discussed above, the first compartment 104(1) may include the pump(s) 116, the tank(s) 112, the gas exchanger 114, and/or the user interface 132. The second compartment 104(2) includes the rotor assembly 106 and the turntable assembly 118, while the third compartment 104(3) includes the motor(s) 108.

A supply line 200 and a discharge line 202 are shown routing to the rotor assembly 106. The supply line 200 and the discharge line 202 may represent some of the fluid lines 120 routed throughout the CBR 100. In some instances, the supply line 200 supplies fresh and recycled medium to the reaction chambers within the rotor assembly 106. For example, the first compartment 104(1) may house a fresh medium tank 206 that contains nutrients for the immunotherapy cells. The supply line 200 may deliver such nutrients to the immunotherapy cells within the rotor assembly 106.

Additionally, the discharge line 202 discharges spent medium from the rotor assembly 106. The supply line 200 and the discharge line 202 may be routed as a bundle of fluid lines into, and from, the rotor assembly 106.

The discharge line 202 may discard the spent medium to a spent medium tank 204 within the first compartment 104(1). In some instances, some of the spent medium discharged from the rotor assembly 106 is mixed with the fresh medium for being reintroduced into the rotor assembly 106. As such, the supply line 200 may additional supply recycled medium to the rotor assembly 106.

The rotor assembly 106 is shown coupled to the turntable assembly 118. The turntable assembly 118 may provide a platform or base to which the rotor assembly 106 couples. In some instances, the supply line 200 and/or the discharge line 202 are routed at least partially through the turntable assembly 118. In some instances, the turntable assembly 118 include one or more rotary unions, or anti-twist mechanisms for preventing twisting of the supply line 200 and/or the discharge line 202 during rotation of the turntable assembly 118 and the rotor assembly 106. The discharge line 202 discards spent medium from the reaction chambers into the spent medium tank 204. The supply line 200, meanwhile, supplies fresh and recycled medium into the reaction chambers.

The turntable assembly 118 is shown including a first pulley 208 around which a belt 210 wraps. The belt 210 additionally wraps around a second pulley 212 of the motor(s) 108. The belt 210 transfers rotational motion of the motor(s) 108 to the turntable assembly 118. Gears and/or other mechanisms may be used to transfer rotation of the motor(s) 108 to the turntable assembly 118.

Figure 3:
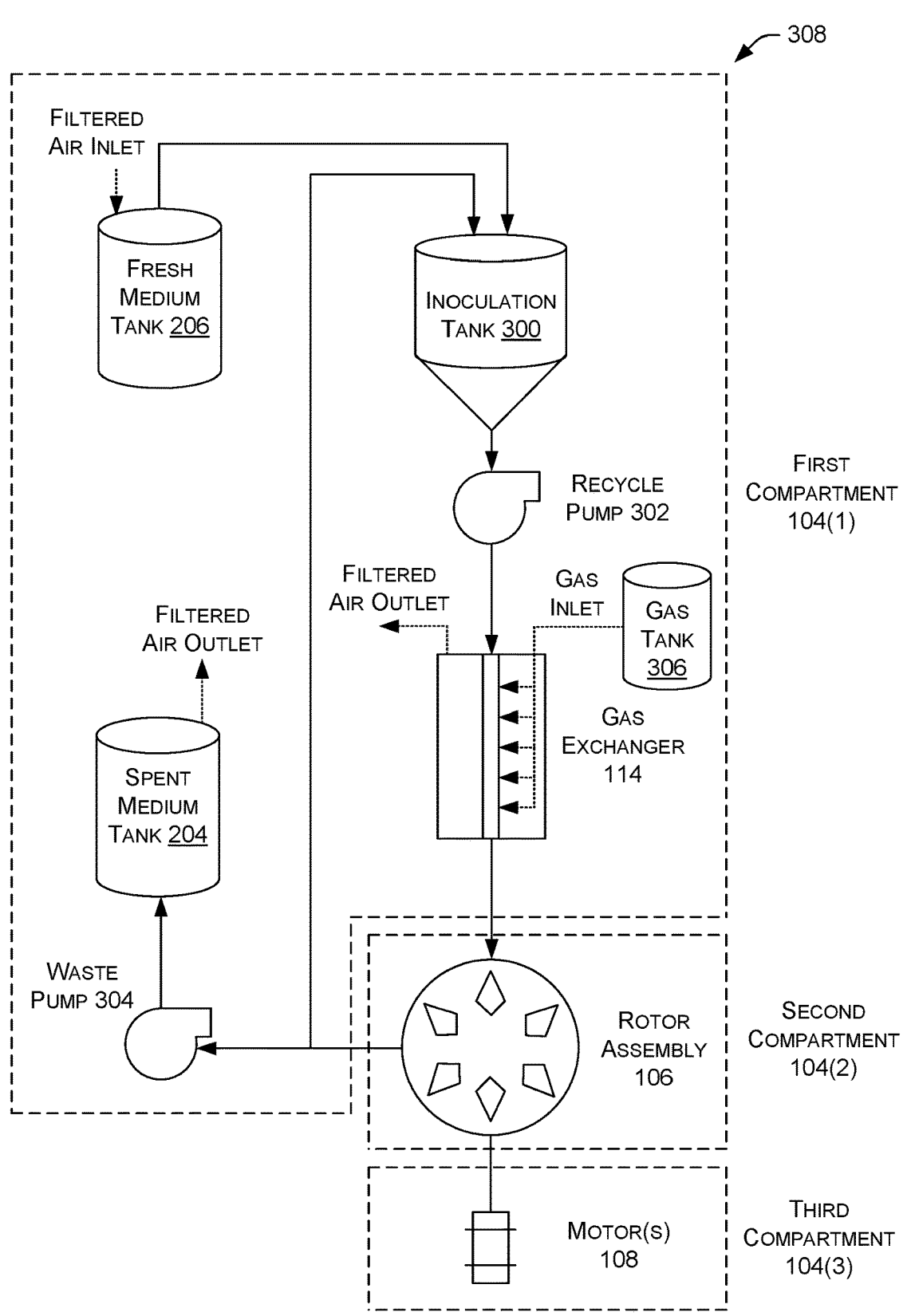
FIG. 3 illustrates a fluid and component diagram of the CBR of FIG. 1, according to an example of the present disclosure.

FIG. 3 illustrates a fluid diagram 308 of the CBR 100 showing additional components of the CBR 100. As discussed above, the first compartment 104(1) may include one or more tank(s) 112, such as the spent medium tank 204, the fresh medium tank 206, as well as an inoculation tank, and/or. The fresh medium tank 206 holds nutrients supplied to the immunotherapy cells. Example nutrients include, for example, A, B, C. As also shown, filtered air is supplied into the fresh medium tank 206. The inoculation tank 300, as explained in further detail, combines the fresh medium from the fresh medium tank with recycled medium from the reaction chambers. The spent medium tank 204 receives waste medium from the reaction chambers. The spent medium tank is shown including a filtered air outlet for venting or exhausting gases that build up within the spent medium tank 204. Such air may be filtered for removing odors, pathogens, and the like.

The first compartment 104(1) is further shown including a recycle pump 302 and a waste pump 304. The recycle pump 302 is fluidly connected to the inoculation tank 300 and the gas exchanger. The recycle pump 302 supplies the fresh and recycled medium to the reaction chambers. The waste pump 304, meanwhile, directs waste medium to the spent medium tank 204. In some instances, the recycle pump 302 may control a flow of fresh and recycled medium into the reaction chambers to balance centrifugal forces acting on the immunotherapy cells in order to suspend the cells within the reaction chambers. In some instances, the waste pump 304 controls an amount of recycled feed exiting the reaction chambers into the inoculation tank 300.

Additionally, within the first compartment, the gas exchanger 114 supplies air or oxygen gas to the fresh and recycled medium that is being pumped by the recycle pump 302. For example, the fresh and recycled medium may be routed through a chamber, tube, or other channel that extends through the gas exchanger 114. As the fresh and recycled medium passes through the gas exchanger 114, the fresh and recycled medium is exposed to the gas. In some instances, the gas includes carbon dioxide (e.g., 5 percent $CO_2$) and oxygen for cell metabolism and growth. The gas is received via a gas tank 306. As also shown in the gas exchanger 114, air is filtered outlet, such as the carbon dioxide that is exposed to the fresh and recycled medium.

The rotor assembly 106 is shown residing within the second compartment 104(2). The turntable assembly 118 may further reside in the second compartment 104(2). The rotor assembly 106 includes reaction chambers in which immunotherapy cells are supplied with the fresh and recycled medium. For example, the rotor assembly 106 receives the fresh and recycled medium after passing through the gas exchanger 114. The fresh and recycled medium feeds the immunotherapy cells for fostering growth. The rotor assembly 106 is rotated via the motor(s) 108 in the third compartment 104(3). In some instances, the motor(s) 108 couple to the rotor assembly 106 or the turntable assembly 118, via a belt. In some instances, the motor(s) 108 is/are configured to rotate the rotor assembly between approximately 600 RPM to approximately 1500 RPM.

In some instances, the first compartment 104(1), the second compartment 104(2), and the third compartment 104(3) are sealed from one another to prevent contamination of the immunotherapy cells and reduction of cell growth. For example, air within the third compartment 104(3) may not be filtered, and if such unfiltered air was permitted to enter the second compartment 104(2), growth of the immunotherapy cells may be adversely impacted. As an additional example, heat generated from the motor(s) 108 may adversely impact growth of the immunotherapy cells with the rotor assembly 106. As such, the compartments 104 may be sealed and insulated from one another.

As shown, fluid lines are routed between the various components of the CBR 100. For example, the fresh medium tank 206 fluidly connects to the inoculation tank 300, the recycle pump 302 fluidly connects to the inoculation tank 300 and the gas exchanger 114, and the gas exchanger 114 fluidly connects to the rotor assembly 106. Such fluid lines channel fresh and recycled medium to the reaction chambers. Additionally, the rotor assembly 106 fluidly connects to the waste pump 304, which in turn is fluidly connected to the spent medium tank 204. The inoculation tank 300 is further shown fluidly connected to the rotor assembly 106 for receiving recycled medium from the reaction chambers.

The inoculation tank 300 represents a location at which fresh medium is mixed with recycled medium. For example, the recycled medium may preserve glucose levels within the medium that is supplied to the immunotherapy cells. As such, resources may be preserved. In addition, by combining fresh medium with the recycled medium, lactate and/or ammonium within the recycled medium may be diluted to levels that are safe for the immunotherapy cells.

In some instances, a certain percentage of the spent medium may be recycled back into the inoculation tank 300. A valve or bypass, for example, may be used to channel some of the spent medium into the inoculation tank 300. In some instances, spent medium is supplied into the inoculation tank 300 at a rate of between approximately 0.40 milliliters per minute (mL/min) to approximately 1.50 mL/min. In addition, fresh medium may be supplied into the inoculation tank 300 at a rate of between approximately 0.020 mL/min to approximately 0.150 mL/min. Other ranges, however, are envisioned.

The CBR 100 may include fittings, couplers, connectors, valves, and the like for fluidly connecting the various components of the CBR 100. Additionally, the valve(s), pump(s) 116, motor(s) 108, and so forth are configured to be controlled via signals or instructions received from the processor(s) 122, for example, or other controllers of the CBR 100. Although the pump(s) 116 are shown at a certain position within the fluid diagram 308, the pump(s) 116 may be located elsewhere. For example, the recycle pump 302 may be located prior to the inoculation tank 300.

Figure 4:
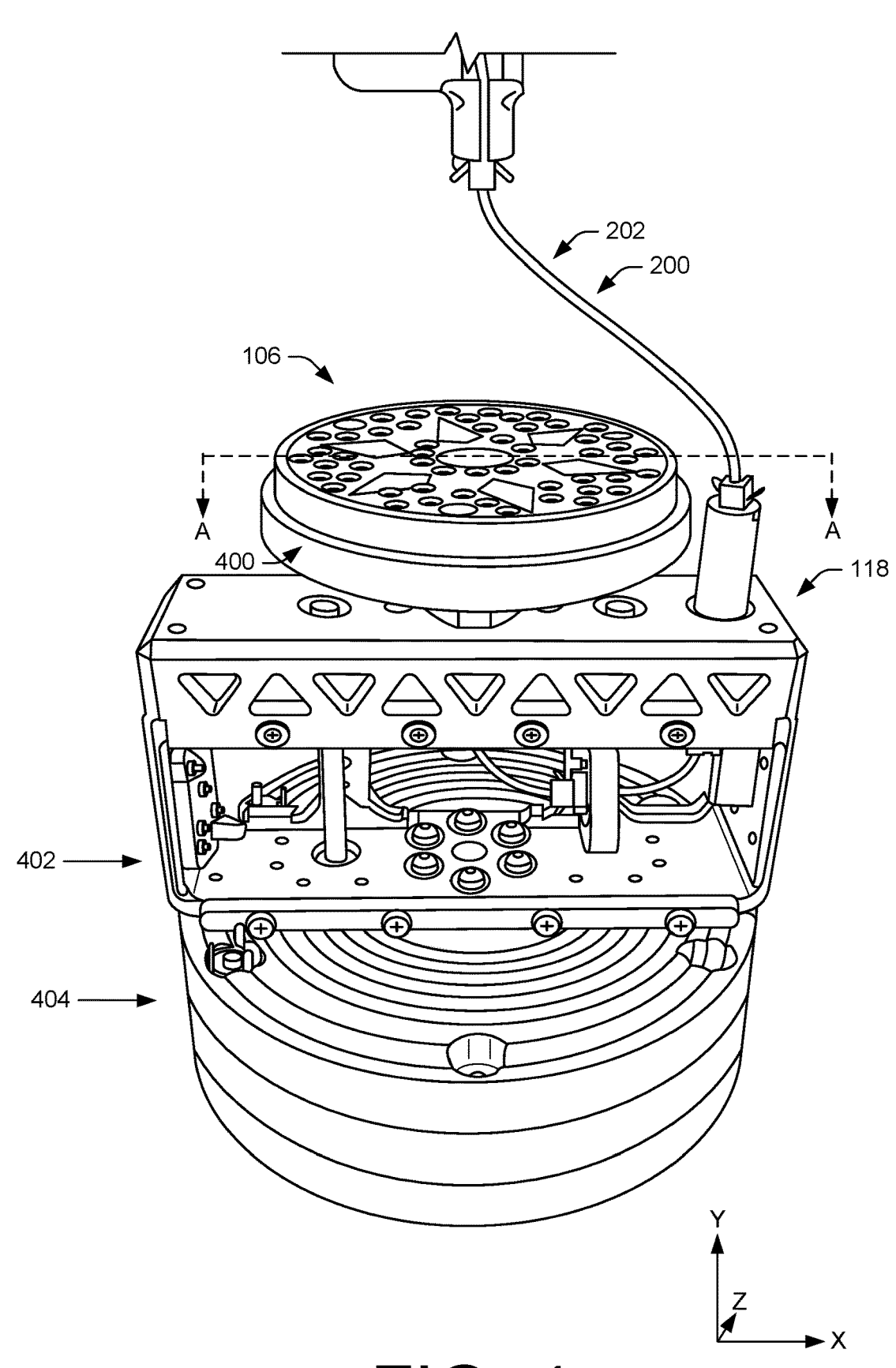
FIG. 4 illustrates an example rotor assembly and turntable assembly of the CBR of FIG. 1, according to an example of the present disclosure.

FIG. 4 illustrates the rotor assembly 106 and the turntable assembly 118. The rotor assembly 106 may be disposed within a receptacle 400 of the turntable assembly 118. The receptacle 400 may include a bowl-like structure within which at least a portion of the rotor assembly 106 resides. The rotor assembly 106 couples within the receptacle 400 for securing the rotor assembly 106 to the turntable assembly 118.

The turntable assembly 118 may include a frame 402 and a disc 404. The frame 402 is shown coupled to the disc 404. During rotation, both the frame 402 and the disc 404 may rotate (e.g., about the Y-axis). The supply line 200 and discharge line 202 are shown extending into the frame 402 of the turntable assembly 118 for routing to the rotor assembly 106. As the CBR 100 rotates, the supply line 200 and the discharge line 202 may correspondingly rotate. As discussed herein, anti-twist mechanisms may prevent twisting of the supply line 200 and the discharge line 202.

Figure 5:
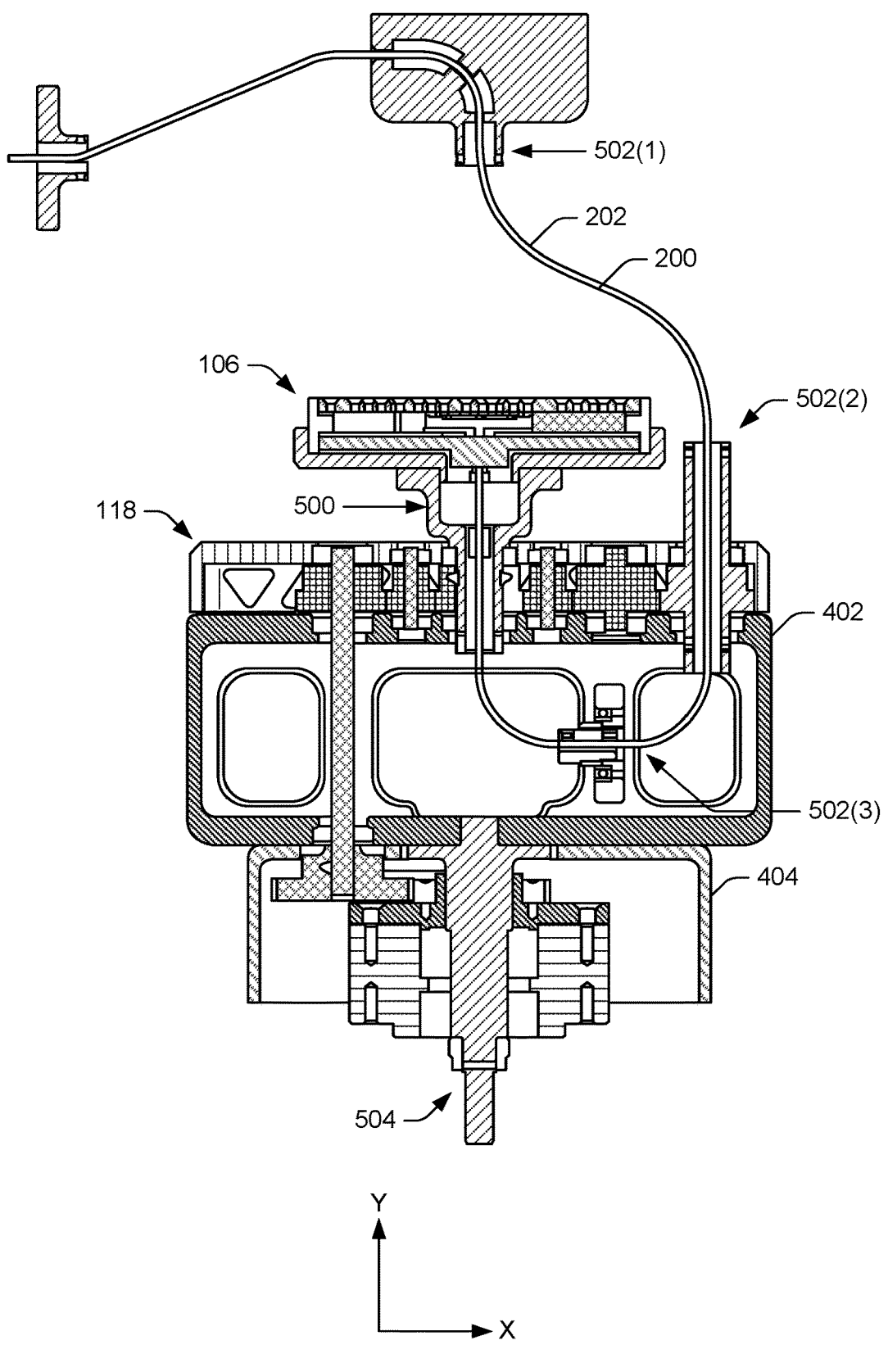
FIG. 5 illustrates a cross-sectional view of the rotor assembly of FIG. 5, taken along line A-A of FIG. 4, according to an example of the present disclosure.

FIG. 5 illustrates a cross-sectional view of the rotor assembly 106 and the turntable assembly 118, taken along line A-A of FIG. 4. The rotor assembly 106 is shown mounted atop the turntable assembly 118. In some instances, the turntable assembly 118 includes the frame 402 to which the rotor assembly 106 mounts. The frame 402 is shown mounted atop the disc 404 (e.g., rotor).

Additionally, the frame 402 may route the supply line 200 and the discharge line 202 to the rotor assembly 106. For example, the supply line 200 may route from the first compartment 104(1) into the second compartment 104(2), overhead of the rotor assembly 106. The supply line 200 may therein route around the rotor assembly 106, into the turntable assembly 118, and then up through a central channel 500. In the central channel 500, the supply line 200 disperses the fresh and recycled medium to the reaction chambers in the rotor assembly 106 (e.g., via manifolds). The discharge line 202 may follow a similar path and fluidly connect to the reaction chambers for receiving the spent medium. The supply line 200 and the discharge line 202 therefore branch out to supply the fresh and recycled medium to, as well as receive the spent medium from, the reaction chamber. In some instances, the supply line 200 and/or the discharge line 202 may be routed differently than shown. For example, the supply line 200 and/or the discharge line 202 may be routed in an inverted fashion out a bottom of the turntable assembly 118 through the frame 402 and/or the disc 404.

The CBR 100 may include one or more anti-twist mechanisms 502, such as rotary unions or anti-twisters. The anti-twist mechanisms 502 prevent twisting of the supply line 200 and the discharge line 202 during rotation of the rotor assembly 106 and the turntable assembly 118. A first anti-twist mechanism 502(1) is shown mounted atop the second compartment 104(2), overhead of the rotor assembly 106. A second anti-twist mechanism 502(2) is shown mounted laterally to the rotor assembly 106. The second anti-twist mechanism 502(2) may extend into, or be a component of, the turntable assembly 118. As shown, the supply line 200 and the discharge line 202 extend between the first anti-twist mechanism 502(1) and the second anti-twist mechanism 502(2). In some instances, the first anti-twist mechanism 502(1) and the second anti-twist mechanism 502(2) are oriented in substantially the same direction. A third anti-twist mechanism 502(3) is shown positioned below the rotor assembly 106, within the turntable assembly 118. The third anti-twist mechanism 502(3) may be oriented substantially perpendicular to the second anti-twist mechanism 502(2). After the third anti-twist mechanism 502(3), the supply line 200 and the discharge line 202 route through the central channel 500 for fluidly connecting to the rotor assembly 106.

In some instances, the turntable assembly 118 includes counterweights for ensuring level rotation of the rotor assembly 106 and the turntable assembly 118. Bearings may also be used to reduce friction during rotation. The turntable assembly 118 is further shown coupled to a shaft 504, which may in turn, be coupled to the first pulley 208 for imparting rotational movement to the CBR 100. The shaft 504 may couple to the frame 402 and/or the disc 404. Additionally, although a single rotor assembly 106 is shown coupled to the turntable assembly 118, additional rotor assemblies 106 may couple to the turntable assembly 118 and/or other rotor assemblies 106. For example, a second rotor assembly may be placed on top of the rotor assembly 106 shown in FIG. 5.

Figure 6A:
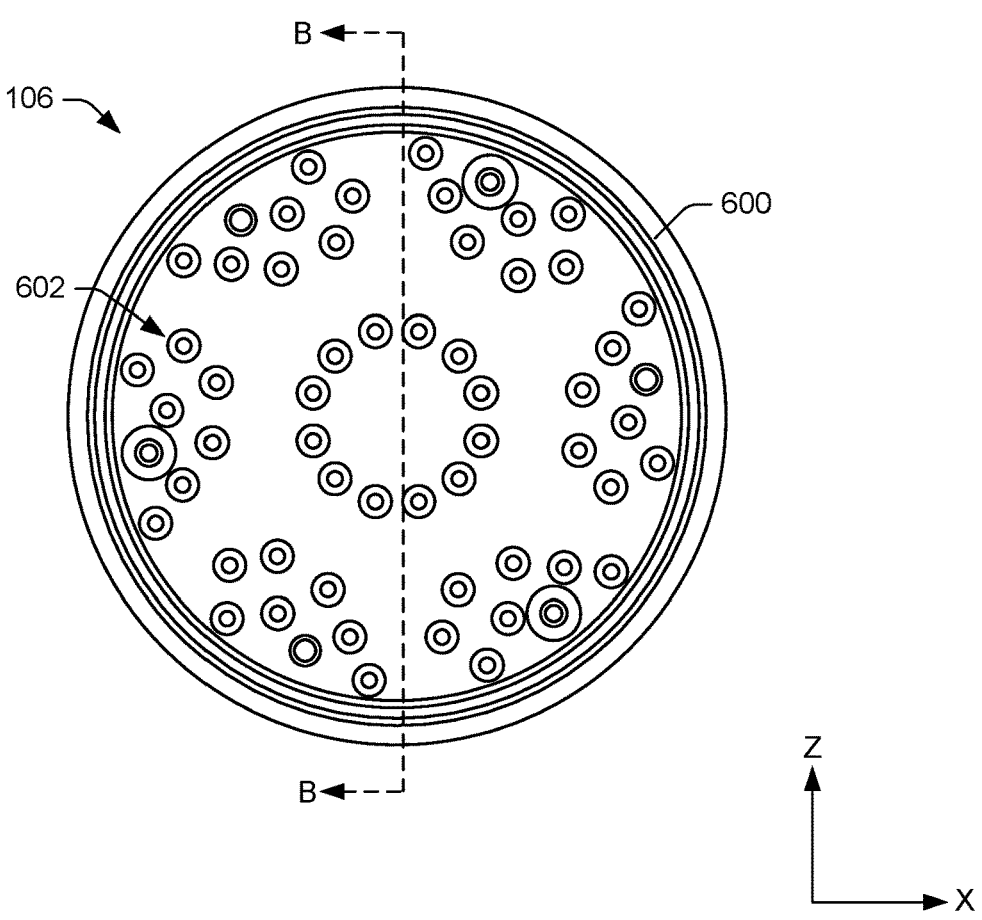
FIG. 6A illustrates a top view of the rotor assembly of FIG. 5, according to an example of the present disclosure.

FIG. 6A illustrates a top view of the rotor assembly 106. The rotor assembly 106 is shown including a top plate 600 that couples to a central disc that defines one or more reaction chambers, as discussed herein. The top plate 600 is shown including a plurality of passages 602 for coupling the top plate 600 to additional components of the rotor assembly 106 (e.g., the central disc). The plurality of passages 602 may further secure the rotor assembly 106 to the turntable assembly 118.

In some instances, the rotor assembly 106 may be interchangeable (e.g., swappable, replaceable, etc.) with other rotor assemblies. For example, the rotor assembly 106 may be uncoupled from the turntable assembly 118, and another rotor assembly 106 may be coupled to the turntable assembly 118. The interchangeable nature of the rotor assemblies 106 may permit increased immunotherapy cell culturing, lessened down time between immunotherapy cell culturing for different patients, and/or reduced risks of contamination.

As an example, a first rotor assembly may be associated with culturing cells for a first patient. After sufficient culturing, the first rotor assembly may be removed, and a second rotor assembly associated with culturing cells for a second patient may be coupled to the turntable assembly 118. This interchange allows for increased cell culturing as the first rotor assembly may be processed, and the cells for the first patient may be extracted once removed from the CBR 100. Of course, it is to be understood that other components of the CBR 100 may be sanitized, disinfected, and the like in between culturing cells of different patients. For example, the supply line 200, the discharge line 202, the pump(s) 116, and the like may be flushed with sanitizer or disinfectants before culturing cells of a different patient. Additionally, or alternatively, contaminated fluid components (e.g., the tank(s)) may be interchangeable. Additionally, or alternatively, pressurized steam (autoclave), or a steam flush, may be used to sterilize components of the CBR 100.

A line B-B is further disposed through the rotor assembly 106. As discussed in FIG. 9A, a cross-sectional view of a reaction chamber, taken through line B-B, is shown.

Figure 6B:
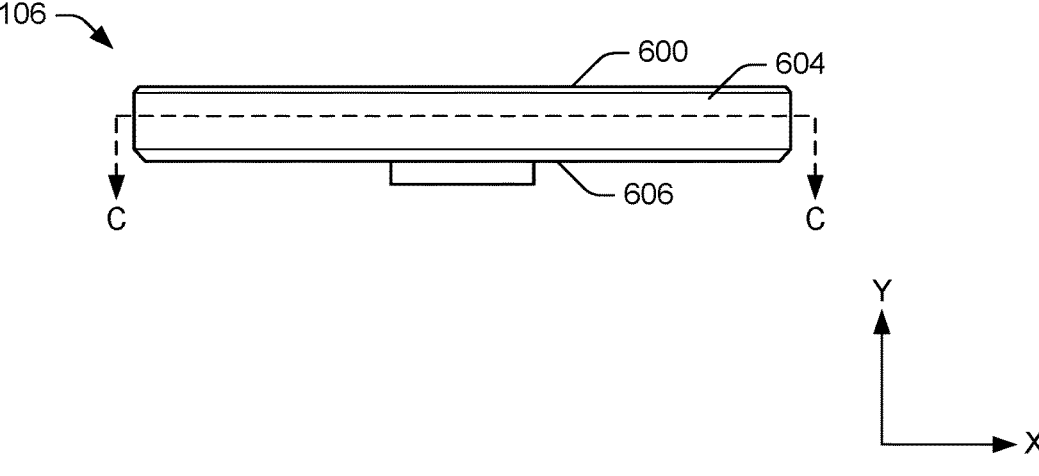
FIG. 6B illustrates a side view of the rotor assembly of FIG. 5, according to an example of the present disclosure.

FIG. 6B illustrates a side view of the rotor assembly 106. In some instances, the rotor assembly 106 is formed at least in part by the top plate 600, a central disc 604, and a bottom plate 606. The top plate 600, the central disc 604, and the bottom plate 606 may couple to one another for at least partially enclosing reactions chambers formed within the central disc 604. In such instances, the top plate 600 may couple to the central disc 604, and the bottom plate 606 may couple to the central disc 604.

In some instances, the rotor assembly 106, or the top plate 600, the central disc 604, and/or the bottom plate 606 are manufactured from plastics, composites, metal, and/or any combination thereof. Rubber or silicon gaskets, for example, may be used to seal components or compartments 104 of the CBR 100. Suitable manufacturing techniques, such as injection molding, stamping, and the like may be used. In some instances, the top plate 600, the central disc 604, and/or the bottom plate 606 may be manufactured from a transparent material for allowing visual observation within the reaction chambers, or the cell cultures within the reaction chambers.

Additionally, although not shown, in some instances, the central disc 604 may include an extraction passage fluidly coupled to the reaction chambers. During culturing of the immunotherapy cells, the cells may be extracted from within the reaction chambers and without removing the rotating assembly from the CBR 100. In some instances, a syringe or other extraction device may be placed through the extraction passage for drawing the immunotherapy cells out of the reaction chambers. The extraction passage permits continuous harvest of the immunotherapy cells while culturing continues.

A line C-C is further disposed through the rotor assembly 106. As discussed in FIG. 9B, a cross-sectional view of a reaction chamber, taken through line C-C, is shown.

Figure 7:
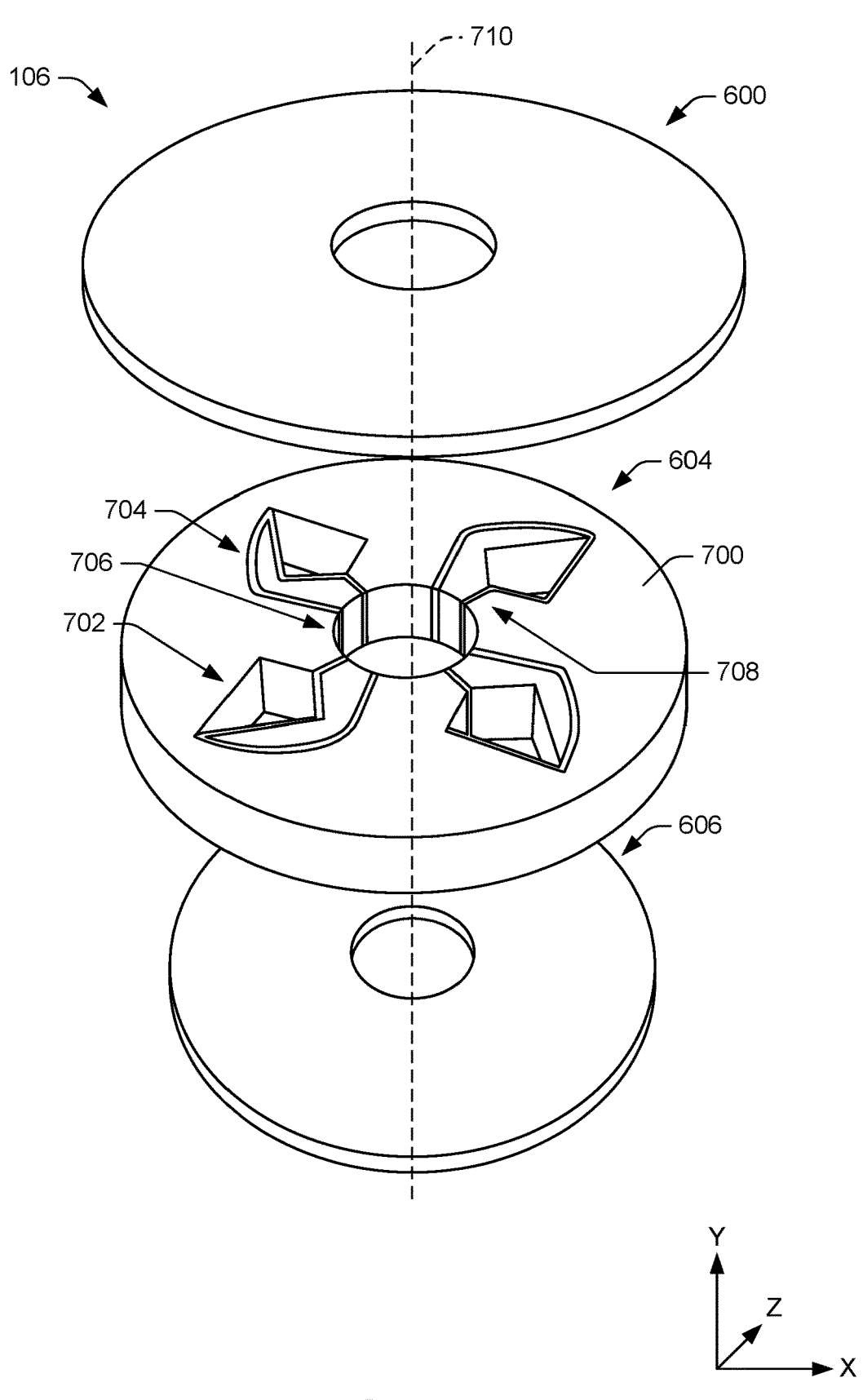
FIG. 7 illustrates an exploded view of the rotor assembly of FIG. 5, according to an example of the present disclosure.

FIG. 7 illustrates an exploded view of the rotor assembly 106. The rotor assembly 106 is shown including the top plate 600 and the bottom plate 606, as well as the central disc 604 interposed between the top plate 600 and the bottom plate 606. When assembled, the top plate 600 couples to a first surface of the central disc 604 and bottom plate 606 couples to a second surface (opposite the first surface) of the central disc 604. For example, the top plate 600 and the bottom plate 606 may be secured to the central disc 604 via fasteners (e.g., screws, bolts, etc.), snap fits, compression, adhesives, and so forth.

The central disc 604 includes a body 700 that defines reaction chambers 702 as well as conduits that fluidly connect to the reaction chambers, respectively. For example, the central disc 604 is shown including four reaction chambers 702. The reaction chambers 702 may extend through a thickness of the body 700 (e.g., in the Y-direction). The reaction chambers 702 are shown including an isosceles trapezoid shape (e.g., kite-like shape) on the X-Z plane. As discussed herein, the shape of the reaction chambers 702 serves to suspend the cells within the reaction chambers 702 (e.g., in the X and Z directions).

The central disc 604 (or the body 700) defines conduits that fluidly couple to the reaction chambers. For example, first conduits 704 (inlet channels) are shown routing from a central passage 706 of the central disc 604, towards an outer periphery of the reaction chambers 702, respectively. The first conduits 704 are formed by the body 700, and route alongside or laterally to the reaction chambers 702 to the outer periphery of the reaction chambers 702, respectively. As discussed in further detail herein, the first conduits 704 route fresh and recycled medium from the supply line 200 to cells within the reaction chambers 702.

Additionally, second conduits 708 (outlet channels) are shown routing from an inner periphery of the reaction chambers 702 to the central passage 706 of the central disc 604. The second conduits 708 are formed by the body 700 and route from the inner periphery of the reaction chambers 702 to the central passage 706, respectively. As discussed in further detail herein, the second conduits 708 route spent or discarded medium from the reaction chamber 702 to the spent medium tank 204. The first conduits 704 and/or the second conduits 708 may extend through a thickness of the central disc 604 or less than a thickness of the central disc 604 (Y-direction). However, in some instances, the first conduits 704 and/or the second conduits 708 may be formed external to the central disc 604, such as separate tubes (external conduits, tubes, etc.) that are not formed in the body 700 of the central disc 604.

The reaction chambers 702 are encased on lateral sides by sidewalls and/or surfaces of the body 700, and on the top and bottom by the top plate 600 and the bottom plate 606, respectively. As such, when the rotor assembly 106 is assembled, the reaction chambers 702 are enclosed by the body 700, the top plate 600, and the bottom plate 606. Additionally, the top plate 600 and the bottom plate 606 serve to define the first conduits 704 and/or the second conduits 708. When assembled, the top plate 600, the bottom plate 606, and the central disc 604 are concentrically aligned with one another, about a central axis 710 of the rotor assembly 106.

The top plate 600, the bottom plate 606, and the central disc 604 are shown being circular in shape, however, other shapes are envisioned (e.g., square, hexagonal, ovular, etc.). The central disc 604 may include, or the body 700 may define, more than or less than four reaction chambers 702. In some instances, the central disc 604 may include an equal amount of reaction chambers to balance the central disc 604 during rotation. In such instances, the reaction chambers 702 may be diametrically opposed from one another. Such balancing may obviate the need for counterweight or other balance control, and increasing total chamber capacity within the same rotor volume.

At the central passage 706, the first conduits 704 may fluidly connect to the supply line 200 via one or more anti-twist mechanisms and/or manifolds. Here, the fresh and recycled medium may be routed to the first conduits 704, respectively, for supplying nutrients to the cells. Similarly, the second conduits 708 may fluidly connected to the discharge line 202 via one or more anti-twist mechanisms and/or manifolds. Here, the spent medium may be routed from to the discharge line 202, via the second conduits 708, for discharging the spent medium from the reaction chambers 702. The top plate 600 and the bottom plate 606 are further shown including passages to accommodate routing of the supply line 200 and the discharge line to the first conduits 704 and the second conduits 708.

Although the rotor assembly 106 is shown and described as being three parts assembled together, in some instances, the rotor assembly 106 may include more than or less than three parts. For example, the rotor assembly 106 may represent a two-part structure.

Figure 8A:
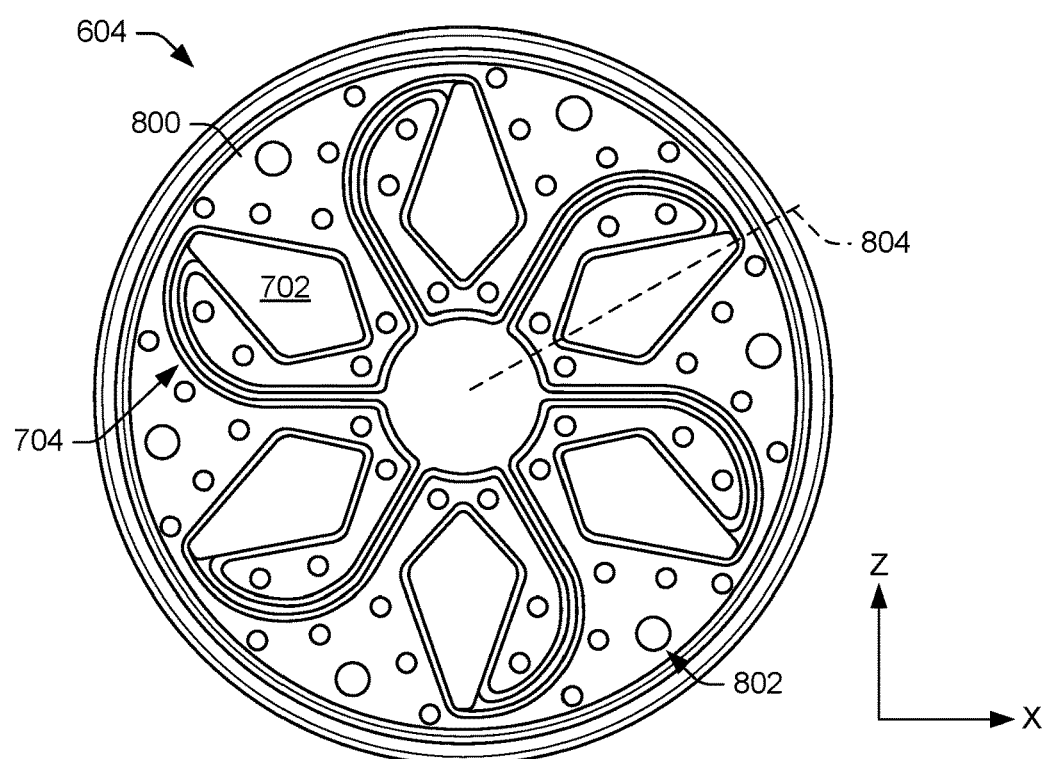
FIG. 8A illustrates a top view of an example central disc of the rotor assembly of FIG. 4, according to an example of the present disclosure.
Figure 8B:
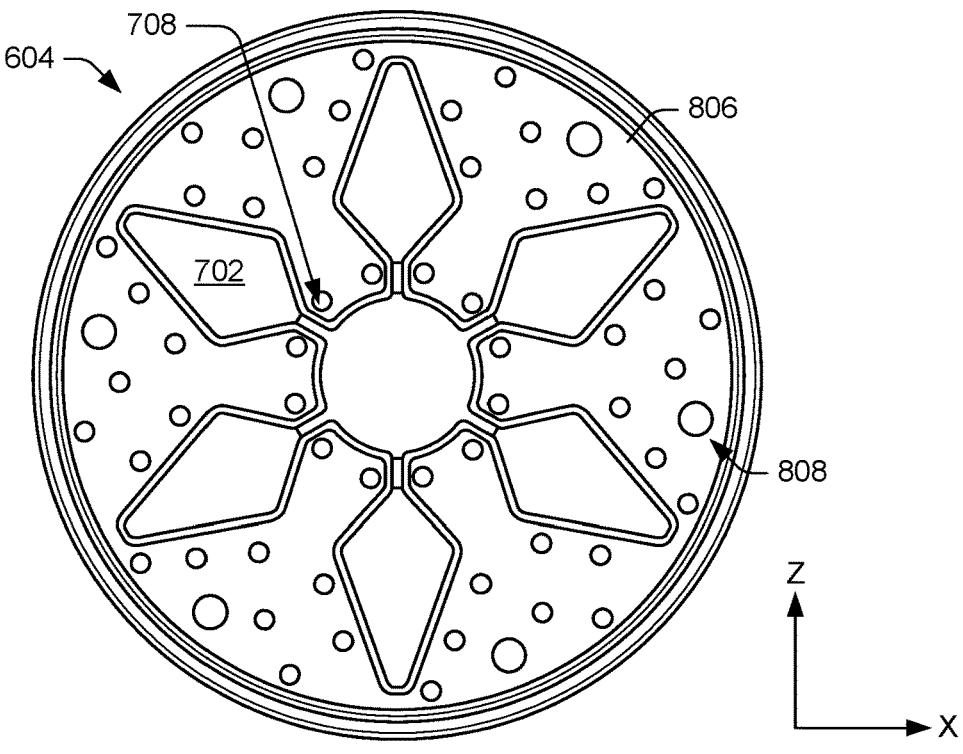
FIG. 8B illustrates a bottom view of the central disc of the rotor assembly of FIG. 4, according to an example of the present disclosure.

FIGS. 8A and FIG. 8B illustrate top and bottom views of the central disc 604, respectively. The central disc 604 in FIGS. 8A and 8B is shown including six reaction chambers 702, as compared to the four reaction chambers shown in FIG. 7. In some instances, the reaction chambers 702 are diametrically opposed form one another, about the central axis 710 of the rotor assembly 106. The diametric position serves to balance the rotor assembly 106 during rotation.

Beginning with FIG. 8A, the central disc 604 (or the body 700) is shown defining the first conduits 704. The first conduits 704 may be formed within, or by, a top surface 800 of the central disc 604. The first conduits 704 extend from the central passage 706 towards an outer edge of the reaction chambers 702, respectively. For example, the first conduits 704 may route alongside a lateral edge of the reaction chambers 702 for fluidly connecting to the reaction chamber 702. Each of the first conduits 704 fluidly connect to the supply line 200 (or one or more supply lines 200). In some instances, a manifold, coupler, unions, and/or other fittings couple to the supply line 200 for dispersing the fresh and recycled medium to the first conduits 704. The supply line 200, as well as the fittings, permit rotation of the rotor assembly 106. For example, the supply line 200 may include anti-twist mechanism to prevent the supply line 200 buckling, twisting, and so forth during rotation. The central disc 604 is further shown including first passages 802 for receiving fasteners that couple the top plate 600 to the central disc 604.

A longitudinal axis 804 is shown disposed through the reaction chambers 702. Each reaction chamber 702 may include a corresponding longitudinal axis 804, and in some instances, the reaction chambers 702 may be symmetrical about the longitudinal axis 804.

Turning to FIG. 8B, the central disc 604 (or the body 700) is shown defining the second conduits 708. The second conduits 708 may be formed within, or by, a bottom surface 806 of the central disc 604. The second conduits 708 extend from the reaction chamber 702, from an inner edge of the reaction chamber 702, towards the central passage 706. Each of the second conduits 708 fluidly connect to the discharge line 202 (or one or more discharge lines 202). In some instances, a manifold, coupler, unions, and/or other fittings couple to the discharge line 202 for discharging the medium from the reaction chambers 702. The discharge line 202, as well as the fittings, permit rotation of the rotor assembly 106. For example, the discharge line 202 may include anti-twist mechanism to prevent the discharge line 202 buckling, twisting, and so forth during rotation. The central disc 604 is further shown including second passages 808 for receiving fasteners that couple the bottom plate 606 to the central disc 604.

Figure 9A:
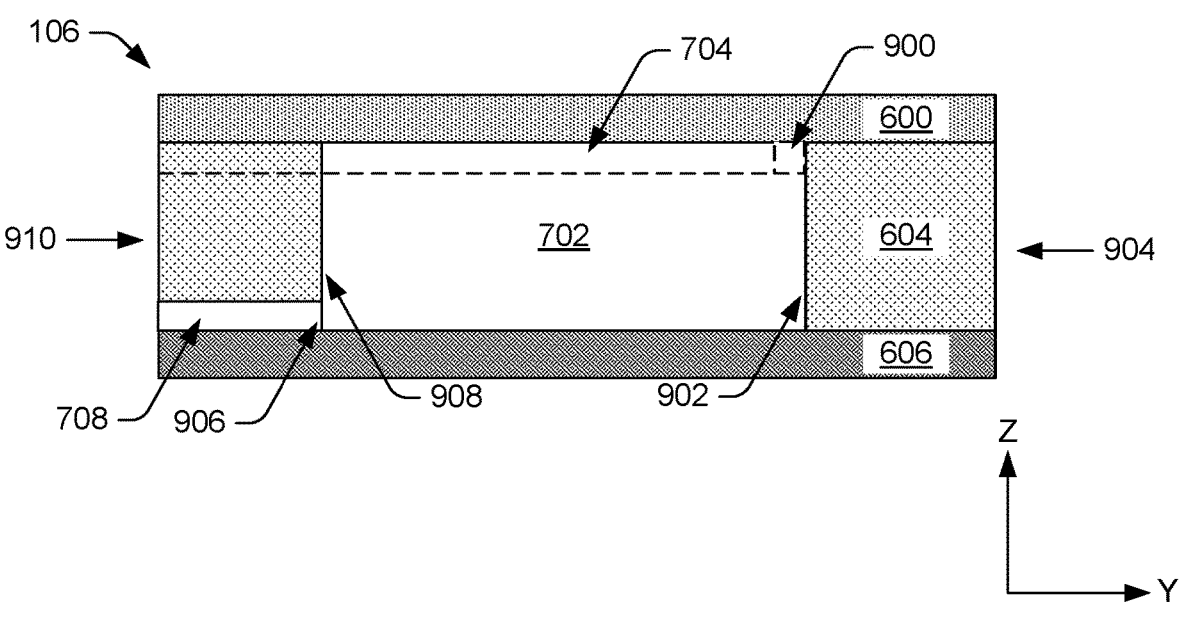
FIG. 9A illustrates a first cross-sectional view of the rotor assembly of FIG. 4, taken along line B-B of FIG. 6A, according to an example of the present disclosure.

FIG. 9A illustrates a partial cross-sectional view of the rotor assembly 106, taken along line B-B of FIG. 6A. In FIG. 9A, a portion of the rotor assembly 106 is shown, such as a half of the rotor assembly 106.

Introduced above, the central disc 604 defines the reaction chambers 702. The first conduits 704 supply medium to the reaction chambers 702. In FIG. 9A, the first conduit 704 is shown in dashed lines to indicate a position of the first conduit 704 behind the reaction chamber 702 (Z direction into the page). That is, the first conduit 704 routes alongside, around the reaction chamber 702. The first conduit 704 includes an inlet 900 for fluidly connecting to the reaction chamber 702. As shown, the inlet 900 may be located at a top of the reaction chamber 702, on an outer edge 902. The outer edge 902 is spaced apart from the central axis 710, towards an outer periphery 904 of the rotor assembly 106. However, the inlet 900 may be located elsewhere, such as at the bottom of the reaction chamber 702, in the middle of the reaction chamber 702 (Z-direction), and so forth. When the top plate 600 couples to the central disc 604, the top plate 600 serves to at least partially define or form the first conduit 704.

Meanwhile, the second conduits 708 discard medium from the reaction chambers 702. The second conduit 708 includes an outlet 906 fluidly connected to the reaction chamber 702. As shown, the outlet 906 may be located at a bottom of the reaction chamber 702, on an inner edge 908. The inner edge 908 is spaced closer to the central axis 710, as compared to the outer edge 902, towards an inner periphery 910 of the rotor assembly 106 (e.g., towards the central axis 710). The inner periphery 910 may represent a portion of the central passage 706. However, the outlet 906 may be located elsewhere, such as at the top of the reaction chamber 702, in the middle of the reaction chamber 702 (Z-direction), and so forth. When the bottom plate 606 couples to the central disc 604, the bottom plate 606 serves to at least partially define or form the second conduit 708.

Noted above, the first conduit 704 fluidly connects to the supply line 200, while the second conduit 708 fluidly connects to the discharge line 202. Although FIG. 9A illustrates a particular cross-sectional shape of the reaction chamber 702, other shapes are envisioned (e.g., circular, trapezoidal, etc.). Moreover, the reaction chamber 702, in some instances, may not extend through a thickness of the central disc 604. Still, although the reaction chamber 702 is shown including a single inlet 900 and a single outlet 906, the reaction chamber 702 may include more than one inlet 900 and/or more than one outlet 906.

When assembled, and as shown in FIG. 9A, the reaction chambers 702 are enclosed (or defined) at least in part by sidewalls of the central disc 604, the top plate 600, and the bottom plate 606. For example, the top plate 600 may enclose (or define) a first side of the reaction chambers 702 (e.g., top), the bottom plate 606 may enclose (or define) a second side of the reaction chambers 702 (e.g., bottom), and the central disc may define lateral sides of the reaction chambers 702. Moreover, the top plate 600 and the bottom plate 606 may respectively define the first conduits 704 and the second conduits 708, respectively. For example, the first conduits 704 and the second conduits 708 may be defined by the central disc 604, and when the top plate 600 and the bottom plate 606 couple to the central disc 604, the top plate 600 and the bottom plate 606 may respectively define the first conduits 704 and the second conduits 708.

Figure 9B:
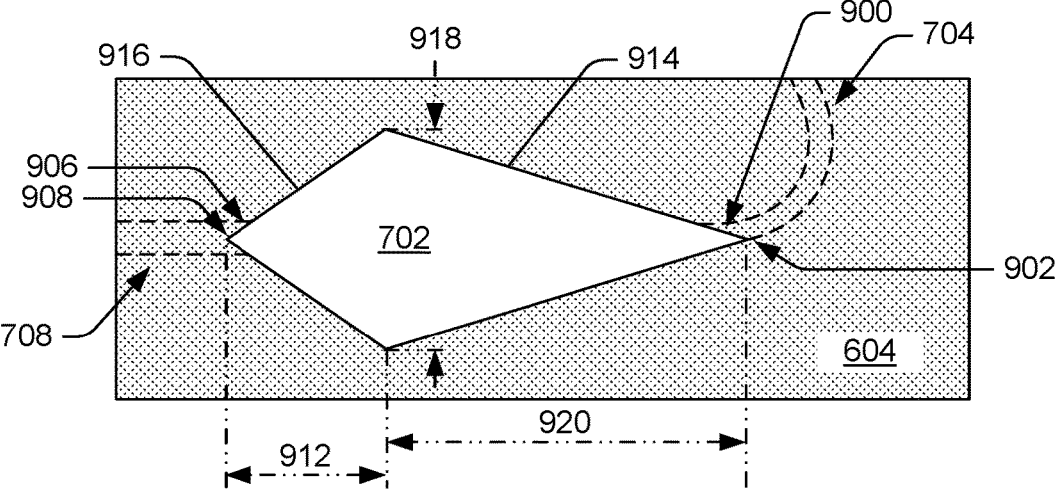
FIG. 9B illustrates a second cross-sectional view of the rotor of the rotor assembly of FIG. 4, taken along line C-C of FIG. 6B, according to an example of the present disclosure.
Figure 9B:
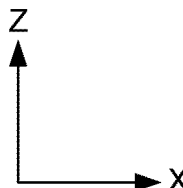

FIG. 9B illustrates a partial cross-sectional view of the rotor assembly 106, taken along line C-C of FIG. 6B. In FIG. 9B, a portion of the rotor assembly 106 is shown, such as a half of the rotor assembly 106.

The central disc 604 defines the reaction chambers 702. In FIG. 9B, the first conduit 704 is shown in dashed lines to indicate a position of the first conduit 704, above a central cross-sectional position of the reaction chamber 702 (Y direction out of the page). A portion of the first conduit 704 is shown in FIG. 9B for fluidly connecting to the reaction chamber 702. As shown, the inlet 900 is located on the outer edge 902, proximate to an outer periphery of the central disc 604. The second conduits 708 are shown in dashed lines to indicate a position of the second conduit 708, below the central cross-sectional position of the reaction chamber 702 (Y direction into the page). As shown, the outlet 906 is located on the inner edge 908, proximate to the inner periphery 910 of the central disc 604.

The reaction chamber 702 is shown including a shape representing an isosceles trapezoid (e.g., kite-like shape) on the X-Z plane. However, other cross-sectional shapes are envisioned (e.g., ovular, circular, square, etc.). The reaction chamber 702 includes a longitudinal length in the X-direction, which in some instances, has a first portion 920 and a second portion 912. The first portion 920 is associated with a first section 914 of the reaction chamber 702, while the second portion 912 is associated with a second section 916 of the reaction chamber 702. The first section 914 is therefore associated with the first portion 920 of the longitudinal length, while the second section 916 is therefore associated with the second portion 912 of the longitudinal length. In some instances, the first portion 920 is longer in length than the second portion 912. However, although relative sizes of the first section 914 and the second section 916 are shown, the first section 914 and/or the second section 916 may be longer than or shorter than shown.

The first section 914 is shown being fluidly connected to the inlet 900, whereas the second section 916 is shown being fluidly connected to the outlet 906. As medium enters the reaction chamber 702, via the inlet 900, a velocity of the fluid decreases as the fluid travels in a direction from the first section 914 to the second section 916. That is, as shown, the first section 914 extends (tapers) outward from the inlet 900 towards the second section 916, away from the longitudinal axis 804 of the reaction chamber 702. A width (Z-direction) of the reaction chamber 702 therefore increases in a direction from the first section 914 to the second section 916. At an intersection between the first section 914 and the second section 916, the reaction chamber 702 has a width 918 (which may represent a greatest width of the reaction chamber 702). The second section 916 extends (tapers) inward towards the outlet 906, towards the longitudinal axis 804 of the reaction chamber 702.

The shape of the reaction chambers 702 serves to suspend the cells within the reaction chambers 702 (e.g., in the X and Z directions). For example, a velocity of the fluid entering the reaction chamber 702 directs the cells in a direction towards the second section 916 (inward towards the central axis 710 of the rotor assembly 106). However, the centrifugal force caused by rotation of the rotor assembly 106 directs the cells in a direction outwards (outward from the central axis 710 of the rotor assembly 106). The centrifugal force is tangential to an axis of rotation of the rotor assembly 106 (e.g., the central axis 710). Suspending the immunotherapy cells within the reaction chambers 702 serves to expose a majority of the immunotherapy cells to the fresh and recycled medium being supplied to the reaction chambers 702. In some instances, a rotational speed of the rotor assembly 106 is adjusted by the motor(s) 108. Adjusting the rotational speed balances centrifugal forces on the immunotherapy cells within the reaction chambers 702 with countervailing hydraulic pressure.

Figure 10:
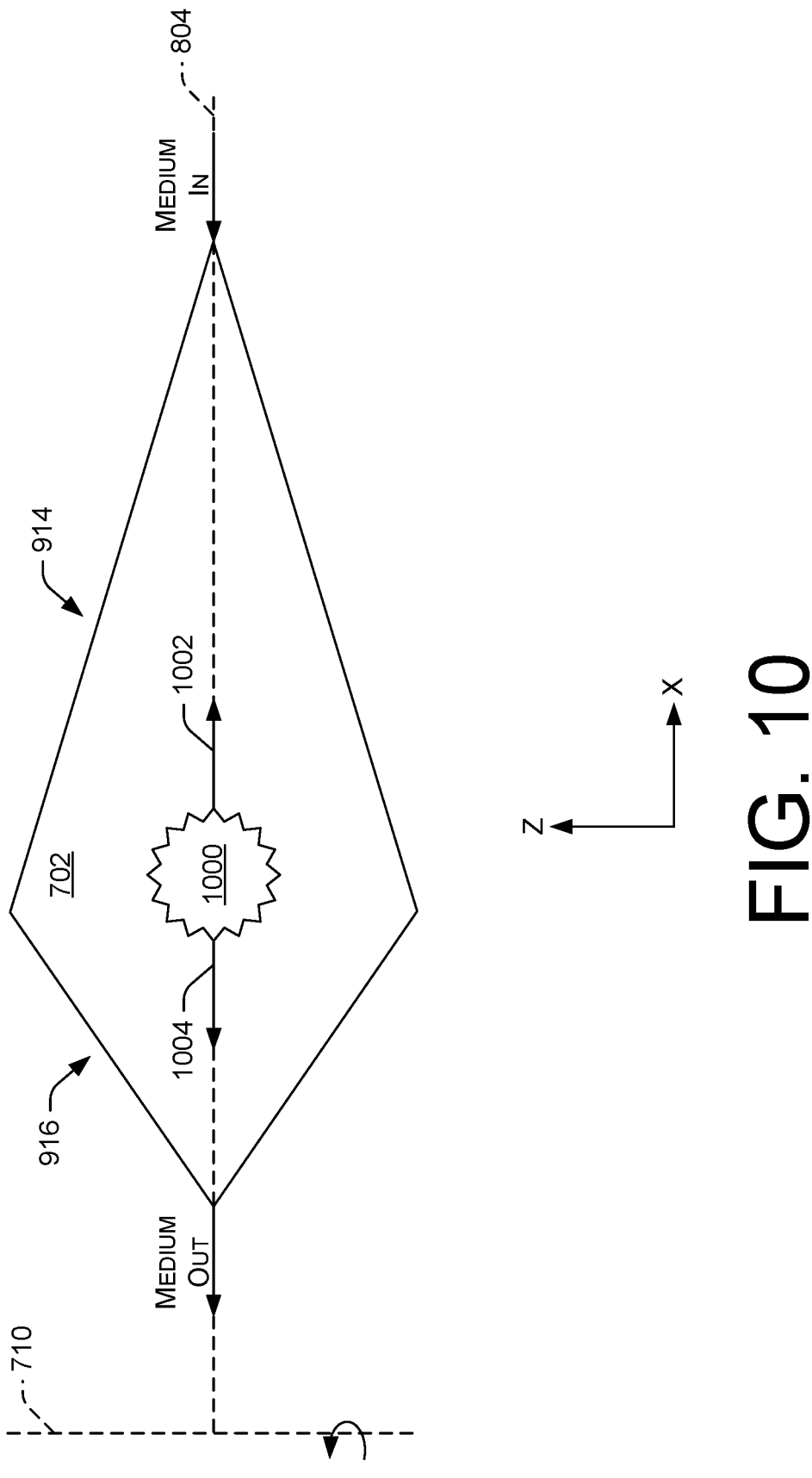
FIG. 10 illustrates an example diagram showing forces acting on a cell culture within a reaction chamber of the rotor assembly, according to an example of the present disclosure.

FIG. 10 illustrates example forces acting on a cell culture 1000 within the reaction chamber 702. The reaction chamber 702 is shown including the kite-like shape for suspending the cell culture 1000 within the reaction chamber (e.g., X-direction), along the longitudinal axis 804. Medium (fresh and recycled) is shown entering the reaction chamber 702 at the outer edge 902, while the medium exits the reaction chamber 702 and the inner edge 908. As the rotor assembly 106 rotates, about the Y-axis, a centrifugal force is applied to the cell culture 1000 in a first direction 1002. The first direction 1002 may be substantially perpendicular to the central axis 710, or the axis about which the rotor assembly 106 rotates. The centrifugal force increases in a direction from the inner edge 908 to the outer edge 902. In addition to the centrifugal force, a drag force and a buoyant force is experienced in a second direction 1004, which is opposite the first direction 1002.

As the medium enters the reaction chamber 702, a velocity of the medium decreases. That is, because of the outward tapering of the reaction chamber 702 along the first section 914, a diameter of the reaction chamber 702 increases to slow the velocity of the medium. In turn, however, given the inward tapering of the second section 916, the velocity of the medium increases towards the outlet 906. That is, the decreasing diameter of the second section 916 results in an increased velocity of the medium. This increased velocity creates the drag force and/or the buoyant force that acts on the cell culture 1000.

As noted above, in some instances, to suspend the cell culture 1000 within the reaction chamber 702 and optimize growth of the cell culture 1000 (e.g., high cell population density), the rotational speed of the rotor assembly 106 (via the turntable assembly 118) may be adjusted and/or the speed of the pump(s) 116 may be increased. This in turn may balance the centrifugal forces with the drag force and the buoyant force. Such balancing suspends the cell culture 1000 within the reaction chamber 702. In turn, cells may be cultured for use in immunotherapy cancer treatment.

FIG. 11 illustrates an example process 1100 for culturing cells within a reaction chamber of a rotating assembly. The process 1100 described herein are illustrated as collections of blocks in logical flow diagrams, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-10, although the process 1100 may be implemented in a wide variety of other environments, architectures and systems.

At 1102, the process 1100 may include combining fresh medium and recycled medium in an inoculation tank. For example, fresh medium from a fresh feed tank may be combined with recycled medium from reaction chambers of a rotor assembly. Within the inoculation tank, the fresh and recycled medium are combined, which as discussed herein, may be supplied to the reaction chambers. In some instances, combining the fresh medium with the recycled medium (or spent medium from the reaction chambers) serves to dilute lactate and ammonium within the medium (which may be harmful to a growth of the cell culture within the reaction chambers). In some instances, a rate at which fresh medium and/or recycled medium is supplied to the inoculation chamber may be based on a speed of one or more pump(s).

At 1104, the process 1100 may include exposing the fresh and recycled medium to gas within a gas exchanger. For example, after the inoculation tank, the fresh and recycled medium may be routed through a gas exchanger, whereby the medium is exposed to oxygen (in an air mixture) for cell metabolism and growth and carbon dioxide (generally 5% of the total mixture) for maintaining a pH level of the fresh and recycled medium. In some instances, the fresh and recycled medium may pass through tubing within the gas exchanger 114 and which is permeable to the carbon dioxide.

At 1106, the process 1100 may include causing the fresh and recycled medium to ebb supplied to reaction chambers of a rotor assembly that contains cell cultures. For example, within the reaction chambers of the rotor assembly, cells may be cultured. The fresh and recycled medium serve to supply nutrients (e.g., feed) to the cell culture to foster growth. In some instances, the fresh and recycled medium may be supplied to any number of reaction chambers within the rotor assembly. For example, a supply line carrying the fresh and recycled medium may branch, split, or otherwise disperse the fresh and recycled medium to the reaction chambers. In some instances, the cell cultures may represent donor cells received from a donor.

At 1108, the process 1100 may include causing a first portion of spent medium to be recycled as the recycled medium and a second portion of the spent medium to be discarded in a spent medium tank. For example, after the fresh and recycled medium passes through the reaction chambers, a discharge line may receive the spent medium. The fresh and recycled medium may become spent medium after passing through the reaction chambers. The discard line may receive the spent medium from the reaction chambers via manifold, for example. A first portion of the spent medium may be recycled back to the inoculation tank, while a second portion of the medium may be discarded in a spent medium tank.

At 1110, the process 1100 may include adjusting at least one of a flow rates of the fresh and recycled medium into the reaction chambers or a rotational speed of the rotor assembly. For example, adjusting the flow rate and/or the rotational speed of the rotor assembly may serve to suspend the cell cultures within the reaction chambers. Centralizing the cell culture may entail balancing a centrifugal force (caused by the rotor assembly rotating) with a drag and buoyant force (caused by the spent medium exiting the reaction chambers). By suspending the cell culture, the cell culture may be exposed to the fresh and recycled medium, which in turn, may lead to increased growth of the cell culture.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A centrifugal bioreactor comprising:
   a turntable assembly;
   an electric motor coupled to the turntable assembly;
   a replaceable rotor assembly coupled to the turntable assembly, the replaceable rotor assembly including a central disc that forms (i) a plurality of reaction chambers configured to house cell cultures and (ii) conduits configured to provide fluid routing to and from the plurality of reaction chambers, respectively;
   a fresh medium tank configured to hold fresh medium for the cell cultures;
   a spent medium tank configured to hold a spent medium produced by the cell cultures;

an inoculation tank configured to combine the fresh medium with a portion of the spent medium;

a gas exchanger configured to expose the fresh medium and the portion of the spent medium to gas;

a first pump fluidly connected to the fresh medium tank, the inoculation tank, and the replaceable rotor assembly, wherein individual reaction chambers of the plurality of reaction chambers are in direct fluid connection with the first pump; and a second pump fluidly connected to the replaceable rotor assembly and the spent medium tank.

2. The centrifugal bioreactor of claim 1, further comprising:

a supply line configured to supply the fresh medium and the portion of the spent medium to the plurality of reaction chambers; and a spent medium line configured to receive the spent medium from the plurality of reaction chambers.

3. The centrifugal bioreactor of claim 1, wherein individual reaction chambers of the plurality of reaction chambers include:

an inlet; and an outlet located closer to a center of the replaceable rotor assembly than the inlet.

4. The centrifugal bioreactor of claim 3, wherein individual reaction chambers of the plurality of reaction chambers are defined at least in part by:

a longitudinal axis extending through the inlet and the outlet;

a first section fluidly connected to the inlet, the first section including sidewalls that extend in a direction away from the longitudinal axis; and a second section fluidly connected to the first section and the outlet, the second section including sidewalls that extend in a direction towards the longitudinal axis.

5. The centrifugal bioreactor of claim 1, further comprising a housing having a first compartment and a second compartment wherein:

the fresh medium tank, the spent medium tank, the inoculation tank, the gas exchanger, the first pump, and the second pump reside in the first compartment; and the turntable assembly and the replaceable rotor assembly reside in the second compartment.

6. The centrifugal bioreactor of claim 1, wherein:

the replaceable rotor assembly includes a top plate and a bottom plate;

the top plate couples to the central disc to enclose the plurality of reaction chambers on a first side; and the bottom plate couples to the central disc to enclose the plurality of reaction chambers on a second side that is opposite the first side.

7. The centrifugal bioreactor of claim 6, wherein the central disc, the top plate, and the bottom plate have a central axis of rotation.

8. The centrifugal bioreactor of claim 1, wherein the central disc encloses the plurality of reaction chambers.

9. The centrifugal bioreactor of claim 1, wherein the plurality of reaction chambers are substantially equal in size.

10. A centrifugal bioreactor comprising:

a rotor assembly including:

one or more layers having a common diameter, a plurality of reaction chambers formed by the one or more layers, the plurality of reaction chambers configured to house cell cultures, and conduits formed by the one or more layers and fluidly connected to the plurality of reaction chambers, the conduits providing fluid routing to and from the plurality of reaction chambers, respectively;

a fresh medium tank configured to hold fresh medium for the cell cultures;

a spent medium tank configured to hold spent medium produced by the cell cultures;

an inoculation tank configured to combine the fresh medium from the fresh medium tank and a portion of the spent medium;

a gas exchanger configured to expose the fresh medium and the portion of the spent medium to gas;

a pump configured to supply the fresh medium and the portion of the spent medium; and a manifold connected to the pump to supply the fresh medium and the portion of the spent medium to individual reaction chambers of the plurality of reaction chambers.

11. The centrifugal bioreactor of claim 10, wherein:

the one or more layers include a top plate, a central disc, and a bottom plate;

the top plate encloses the plurality of reaction chambers on a first side;

the central disc encloses a perimeter of the plurality of reaction chambers; and the bottom plate encloses the plurality of reaction chambers on a second side.

12. The centrifugal bioreactor of claim 10, wherein the one or more layers enclose the plurality of reaction chambers.

* * * * *